US008251919B2

(12) United States Patent
Fukuzawa

(10) Patent No.: US 8,251,919 B2
(45) Date of Patent: Aug. 28, 2012

(54) LANCET AND LANCET DEVICE INCLUDING THE SAME

(75) Inventor: Masahiro Fukuzawa, Kyoto (JP)

(73) Assignee: Arkray, Inc. (JP)

( * ) Notice: Subject to any disclaimer, the term of this patent is extended or adjusted under 35 U.S.C. 154(b) by 323 days.

(21) Appl. No.: 11/664,976

(22) PCT Filed: Oct. 25, 2005

(86) PCT No.: PCT/JP2005/019617
§ 371 (c)(1),
(2), (4) Date: Apr. 9, 2007

(87) PCT Pub. No.: WO2006/046570
PCT Pub. Date: May 4, 2006

(65) Prior Publication Data
US 2009/0012427 A1    Jan. 8, 2009

(30) Foreign Application Priority Data

Oct. 25, 2004    (JP) .................................. 2004-309050

(51) Int. Cl.
*A61B 5/00* (2006.01)
(52) U.S. Cl. ........................................ 600/583; 606/182
(58) Field of Classification Search .................. 600/583; 606/182
See application file for complete search history.

(56) References Cited

U.S. PATENT DOCUMENTS

| 4,990,154 | A | * | 2/1991 | Brown et al. | 606/182 |
| 5,147,375 | A | * | 9/1992 | Sullivan et al. | 606/182 |
| 5,314,442 | A | * | 5/1994 | Morita | 606/182 |
| 5,324,303 | A | * | 6/1994 | Strong et al. | 606/181 |
| 5,628,764 | A |   | 5/1997 | Schraga |   |
| 5,741,288 | A | * | 4/1998 | Rife | 606/181 |
| 2004/0092996 | A1 | * | 5/2004 | List et al. | 606/181 |
| 2004/0102717 | A1 | * | 5/2004 | Qi | 600/583 |
| 2004/0243165 | A1 |   | 12/2004 | Koike et al. |   |

(Continued)

FOREIGN PATENT DOCUMENTS

AU    2003275671 A1    6/2004

(Continued)

OTHER PUBLICATIONS

The Extended European Search Report dated Feb. 18, 2011; Patent Application No. / Patent No. 05805263.0-2319 / 1815792 PCT/JP2005019617.

*Primary Examiner* — Max Hindenburg
*Assistant Examiner* — Renee Danega
(74) *Attorney, Agent, or Firm* — Studebaker & Brackett PC; Donald R. Studebaker

(57) ABSTRACT

In order to provide a lancet which has a simple structure and which can secure safety, in particular, after use, and a lancet device including the same, a lancet (20) includes a casing (22), and a puncture body (23) which is accommodated in the casing (22) so as to be movable in a puncturing direction. For removing the lancet (20) from a main body (30), the lancet (20) has a convex portion (22b) formed on an inner surface (22a) of the casing (22) and a recessed portion (groove (23c)) formed on the puncture body (23), which form fitting for holding the puncture body (23) so as to be immovable in the puncturing direction in the casing (22).

32 Claims, 18 Drawing Sheets

U.S. PATENT DOCUMENTS

| | | |
|---|---|---|
| 2006/0047220 A1 | 3/2006 | Sakata et al. |
| 2009/0088787 A1 | 4/2009 | Koike et al. |

FOREIGN PATENT DOCUMENTS

| | | |
|---|---|---|
| EP | 0595148 | 1/1998 |
| EP | 1671584 | 6/2006 |
| EP | 1 610 682 B1 | 8/2010 |
| JP | 06-133955 | 5/1994 |
| JP | 06-237922 | 8/1994 |
| JP | 2000-245717 | 9/2000 |
| JP | 3144718 | 1/2001 |
| JP | 2004-033438 | 2/2004 |
| JP | 2004-033439 | 2/2004 |
| JP | 2004-057490 | 2/2004 |
| JP | 2004-113580 | 4/2004 |
| JP | 2004-290390 | 10/2004 |
| WO | WO-96/02401 A1 | 2/1996 |
| WO | WO-03/005907 A1 | 1/2003 |
| WO | 2004/043258 A1 | 5/2004 |
| WO | 2004/080305 A1 | 9/2004 |

* cited by examiner

LANCET AND LANCET DEVICE INCLUDING THE SAME

TECHNICAL FIELD

The present invention relates to a lancet used for forming a puncture wound for collecting a body fluid or the like from a skin, and a lancet device including the same.

BACKGROUND ART

In recent years, as the number of diabetic patients increases, the number of diabetic patients who measure their blood glucose levels by themselves at home and self-supervise changes in the blood glucose levels increases. In view of such a situation, for collecting blood for measurement of the blood glucose level, lancet devices (puncture tools) including a puncture needle which can readily wound a fingertip to collect blood necessary for the measurement has been provided.

A lancet device includes a puncture needle on a tip portion. The puncture needle is discharged by utilizing a spring or the like with the tip portion being pressed against a fingertip or the like, and the puncture needle is protruded from the tip portion by about few tenths of a millimeter to 2.0 mm. In this way, the fingertip or the like is cut and blood flowing from the wound is collected. The collected blood is dropped onto a sensor portion or the like of the blood glucose meter to measure the blood glucose level.

Such a lancet device includes the puncture needle for forming a wound on a fingertip or the like of a patient as described above. Thus, patients, particularly, elderly with weakened eyesight and the like may undesirably injure themselves by erroneously handling the puncture needle.

Thus, so-called safety lancet device which employs a structure which does not expose a puncture needle from a main body part when it is not necessary has been proposed (see Japanese Laid-Open Publication No. 2000-245717).

For example, according to Japanese Laid-Open Publication No. 2000-245717, safety is ensured by using two coil springs and defining moduli of elasticity of these springs so that the puncture needle is prevented from protruding outside a casing when it is not needed.

DISCLOSURE OF THE INVENTION

Problems to be Solved by the Invention

However, the above conventional lancet device has following problems.

In the lancet device disclosed in the Japanese Laid-Open Publication No. 2000-245717, the lancet is not securely fixed in the case after use. Thus, if the case is shaken after use, the puncture needle may be unlocked, and the tip of the needle may be protruded outside the case. If the lancet is erroneously re-attached to the case after use, fitting to a puncture needle holder is insufficient, and the tip of the puncture needle may protrude and may be harmful. Thus, it is difficult to say that the safety after use is ensured at a high level.

An object of the present invention is to provide a lancet with a simple structure which can ensure safety after use in particular, and a lancet device including the same.

Means for Solving the Problems

A lancet according to the first invention is a lancet to be attached to a main body portion including a biasing member configured to cause a tip of a puncture needle to protrude in a predetermined puncturing direction, which includes a puncture body, a case portion, and a first fitting portion. The puncture body includes a puncture needle and a connection portion which is formed on an end opposite to the puncture needle and is to be connected to the main body portion. The case portion includes a tubular portion and an opening. The tubular portion accommodates the puncture body so as to be movable back and forth in the puncturing direction. The opening is formed on an end of the puncture needle on the side to protrude. The first fitting portion holds the puncture body in the case portion so as to be immovable back and forth in the puncturing direction when the connection portion of the puncture body is separated from the main body portion.

In such a structure, when the case portion is removed from the main body portion after a puncture wound is formed, the puncture body is held strongly by the first fitting portion so as to be immovable back and forth in the puncturing direction.

The first fitting portion may be a combination of a recessed portion or a convex portion formed on an outer periphery of the puncture body and a convex portion or a recessed portion formed on an inner surface of the tubular portion of the case portion in which the puncture body is accommodated, or the like. In other words, when the lancet of the present invention is removed from the main body, the recessed portion or the convex portion formed on the puncture body and the convex portion or the recessed portion formed on the inner surface of the tubular portion of the case portion fit each other, and the puncture body is strongly held in the case portion so as to be immovable in the puncturing direction.

With such a structure, the puncture needle can be prevented from protruding from the tip of the puncture body when the puncture body is removed from the main body portion and discarded after a puncture wound is formed without putting a cap covering the tip of the puncture needle. As a result, even with a simple structure, a possible danger that the tip of the puncture needle after puncturing erroneously comes out from the main body portion when the lancet is discarded and a user is injured or be infected with a disease by body fluid attached to the used puncture needle can be averted. Further, even the used lancet is erroneously attached to the main body again, since the puncture body is strongly held by the first fitting portion so as to immovable in the puncturing direction once it is removed from the main body portion, the puncture needle is prohibited from being discharged. Thus, the possibility of infection caused by reusing the contaminated needle can be reduced, and the lancet with higher safety can be provided.

The lancet according to the second invention is a lancet of the first invention which further includes a second fitting portion configured to hold the puncture body so as to be immovable back and forth in the puncturing direction before use.

In such a structure, the second fitting portion holds the puncture body before use in the case so as to be immovable back and forth in the puncturing direction.

Thus, since the puncture body can be held so as not to move in the case in the puncturing direction before use, safety before use can also be ensured.

The second fitting portion may be a combination of a recessed portion or a convex portion formed on an outer periphery of the puncture body and a convex portion or a recessed portion formed on an inner surface of the tubular portion of the case portion in which the puncture body is accommodated or the like, similarly to the first fitting portion.

The lancet according to the third invention is a lancet according the second invention in which the second fitting portion is formed by combining a convex portion and a recessed portion formed on a cap portion attached to a front end side of the puncture body so as to cover a tip of the puncture needle and an inner surface of the tubular portion.

In such a structure, the second fitting portion configured to hold the puncture body so as to be immovable in the puncturing direction before use is formed of a set of a convex portion and a recessed portion formed on the cap portion attached to a tip portion of the puncturing body and an inner surface of the tubular portion of the case portion.

Thus, by separating the cap from the tip portion of the puncture body in use, the puncture body can also be disengaged in the puncturing direction.

The convex portion and the recessed portion mentioned above may be the convex portion formed on the cap portion and the recessed portion formed on the inner surface of the tubular portion, or vice versa.

The lancet according to the fourth invention is a lancet of the third invention in which the cap portion is integrally formed with the puncture body.

In such a structure, the cap and the puncture body is integrally formed so that the number of components is decreased in order to reduce the cost.

The lancet according to the fifth invention is a lancet according to any one of the first through fourth inventions in which the first fitting portion has a strong fitting force to prohibit the puncture needle to again move in the puncturing direction.

In such a structure, the first fitting portion has a strong fitting force which is difficult to disengage once fitting is achieved.

Thus, the puncture needle can be securely prohibited from protruding from the tip of the case after use, and a lancet which secures the safety after use in more effective manner can be provided.

The lancet according to the sixth invention is a lancet according to any one of first through fifth inventions in which the first fitting portion holds the puncture body at a position closer to a portion connected to the main body than a standby position of the puncture body immediately before being discharged so that a tip of the puncture needle protrudes from the opening.

In such a structure, the first fitting portion which holds the puncture body so as to be immovable in the puncturing direction when it is removed from the main body portion after use holds the puncture body at a position closer to a connected side to the main body portion than the standby position of the puncture body immediately before being discharged so that the tip of the puncture needle protrudes from the opening.

Thus, the puncture body is movable at the front end side of the case portion when in use, and, after use, the puncture body can be readily held by the first fitting portion by being moving toward the side connected to the main body portion when the puncture body is removed from the main body.

The lancet according to the seventh invention is a lancet according to any one of the first through sixth inventions in which the first fitting portion is formed by combining a convex portion and a recessed portion formed on an outer peripheral surface of the puncture body substantially parallel to the puncturing direction and an inner peripheral surface of the case portion in which the puncture body moves.

In such a structure, by forming a convex portion and a recessed portion or a recessed portion and a convex portion respectively on the outer peripheral surface of the puncture body and the inner peripheral surface of the case portion and combining them, the first fitting can be readily formed.

The lancet according to the eighth invention is a lancet of the seventh invention in which at least one the convex portion and the recessed portion resiliently deforms to fit to each other.

In such a structure, at least one of the convex portion and the recessed portion formed on the outer peripheral surface of the puncture body and the inner peripheral surface to form the first fitting portion resiliently deforms when the puncture body and the case portion are fit to each other.

Thus, the first fitting portion having a structure that is easy to be fitted and difficult to disengage can be formed.

The lancet according to the ninth invention is a lancet according to any one of the first through eighth inventions in which the first fitting portion includes a recessed portion and a convex portion. The recessed portion is formed on an outer periphery of the puncture body and is formed adjacent to a protrusion of a tapered shape becoming narrower toward the side connected to the main body. The convex portion is formed on an inner surface of the tubular portion and fits to the recessed portion.

In such a structure, for removing the used lancet from the main body portion, the puncture body is moved toward the side connected to the main body portion, and the convex portion formed on the inner surface of the tubular portion is fitted to and held by a groove portion formed adjacent to a most protruded portion of a tapered protrusion formed on the outer peripheral portion of the puncture body.

By combining the protrusion of a tapered shape, a fitting portion, which can be readily fitted because a narrow side of the tapered shape is inserted first, but which is difficult to disengage once it is fitted, can be achieved.

The lancet according to the tenth invention is a lancet according to any one of the first through eighth inventions which includes a tapered portion formed on either an outer periphery portion of the puncture body or an inner peripheral surface of the tubular portion.

In such a structure, the tapered portion is formed on either the outer periphery of the puncture body or the inner peripheral surface of the tubular portion of the case portion. Thus, the fitting portion which can be readily fitted and is difficult to disengage can be achieved.

The lancet according to the eleventh portion is a lancet according to any one of the first through eighth inventions in which the first fitting portion includes a convex portion formed on an outer periphery portion of the puncture body, and a recessed portion which is provided adjacent to the tapered portion formed on an inner surface of the tubular portion and fits to the convex portion.

In such a structure, for removing the used lancet from the main body portion, the puncture body is moved toward the side connected to the main body portion, and the convex portion formed on the outer periphery of the puncture body is fitted to and held by a recessed portion formed adjacent to a most protruded portion of a tapered protrusion.

By combining the protrusion of a tapered shape, a fitting portion, which can be readily fitted because a narrow side of the tapered shape is inserted first, but which is difficult to disengage once it is fitted, can be achieved.

The lancet according to the twelfth invention is a lancet according to any one of the first through eighth inventions in which the first fitting portion includes a recessed portion and a convex portion. The recessed portion is formed adjacent to a plurality of protrusions protruding toward a direction orthogonal to the puncturing direction on an outer peripheral surface of the puncture body. The convex portion is formed on an inner surface of the tubular portion and fits to the recessed portion.

In such a structure, for removing the used lancet from the main body portion, the puncture body is moved toward the side connected to the main body portion, and the recessed portion formed adjacent to a plurality of protrusions formed on the outer peripheral portion of the puncture body is fitted to and held by the convex portion formed on the inner surface of the tubular portion of the case portion.

By combining the recessed portion adjacent to the plurality of protrusions formed along the outer periphery of the puncture body and the convex portion formed along the inner surface of the tubular portion, the puncture body can be held at a few points. Thus, a fitting portion, which can be readily fitted and difficult to disengage, can be achieved.

The protrusion of the puncture body may be, for example, a part of a puncture body having a cross section perpendicular to the puncturing direction of a substantially circular shape, particularly the one with a cross section of an ellipsoidal shape. In such a case, since the recessed portion formed adjacent to the protrusions on the long sides of the cross section of the ellipsoidal shape is fitted to the convex portion formed along the inner surface of case portion having the cylindrical shape. Both or one of them resiliently deform and they are readily fitted being held at two points. By combining the puncture body and the case portion respectively having a cross section of a circular shape and an ellipsoidal shape, or vice versa, a fitting portion held at two points can be readily achieved.

The lancet according to the thirteenth invention is a lancet according to any one of the first through eighth inventions in which the first fitting portion includes a plurality of convex portions protruding toward a direction orthogonal to the puncturing direction on an outer peripheral surface of the puncture body; and a recessed portion which is formed on an inner cylindrical surface of the tubular portion and fits to the convex portions.

In such a structure, for removing the used lancet from the main body portion, the puncture body is moved toward the side connected to the main body portion, and the plurality of convex portions formed on the outer peripheral portion of the puncture body are fitted to and held by the recessed portion formed on the inner surface of the tubular portion of the case portion.

By combining the plurality of convex portions formed along the outer periphery of the puncture body and the recessed portion formed along the inner surface of the tubular portion, the puncture body can be held at a few points. Thus, a fitting portion, which can be readily fitted and difficult to disengage, can be achieved.

The lancet according to the fourteenth invention is a lancet according to any one of the first through eighth inventions in which the first fitting portion includes a convex portion which is formed to protrude in a direction orthogonal to the puncturing direction from an outer periphery of the puncture body, and has a cross section cut along a plane perpendicular to the puncturing direction which is an ellipsoidal shape.

In such a structure, the convex portion which forms the first fitting portion may be a portion of the long sides of the cross section having the ellipsoidal shape of the puncture body cut along a plane orthogonal to the puncture direction. Thus, the long side portion of the ellipsoidal shape can be utilized as the convex portion with respect to the circular case portion, and the fitting portion which is fitted at two points in the case portion can be achieved.

The lancet according to the fifteenth invention is a lancet according to any one of the first through fourteenth inventions further including an analysis tool which is attached to an end of the case portion on the front side in the puncturing direction, and analyzes a particular component in body fluid collected from a puncture wound formed by the puncture needle.

With such a structure, body fluid collected from a puncture wound formed by the lancet is detected by an analysis tool such as a biosensor attached to the front end side of the lancet and the measurement of the glucose concentration or the like can be performed.

A lancet device according to the sixteenth invention includes a lancet according to any one of the first through fifteenth inventions, a main body portion and a third fitting portion. The main body portion includes a puncture body holder for holding a rear end side of the puncture body with the lancet being loaded, and a biasing member for discharging the puncture body with the puncture body holder in the puncturing direction. The third fitting portion holds the puncture body and the puncture body holder in the puncturing direction.

In such a structure, the lancet device includes the third fitting portion for fitting puncture body holder for holding the rear end side of the puncture body and the puncture body.

Thus, when the lancet is loaded to the main body portion, the puncture body is held by the puncture body holder via the third fitting portion, and when the lancet is removed from the main body portion after use, the third fitting portion is disengaged and the puncture body is held by the first fitting portion. In this way, the puncture body can be discharged to a predetermined puncture direction when in use, and it can be immovable in the puncture direction after use. Thus, a lancet device with high safety, particularly, after use can be provided.

The third fitting portion may be a combination of a recessed portion or a convex portion formed on the outer periphery of the puncture body, and a convex portion or a recessed portion formed on the inner surface of the puncture holder, or the like, similarly to the first and second fitting portions.

The lancet device according to the seventeenth invention is a lancet device according to the sixteenth invention in which the third fitting portion has a fitting force for holding the puncture body which is weaker than that of the first fitting force.

In such a structure, with the lancet being loaded to main body portion, the fitting force of the third fitting portion which holds the rear end side of the puncture body by the puncture body holder is weaker than the first fitting portion which holds the puncture body in the case when the lancet is removed from the main body portion.

Thus, for removing the lancet from the main body portion after use, when the puncture body which has been held by the puncture body holder at the third fitting portion is moved in the case portion to be held by the first fitting portion, the third fitting is disengaged because the fitting force of the first fitting portion is stronger than that of the third fitting portion. As a result, the puncture body held by the third fitting portion can be smoothly switched to be held by the first fitting portion, and the lancet can be removed from the main body portion such that the tip of the needle does not protrude. Thus, the lancet device with further improved safety can be provided.

The lancet device according to the eighteenth invention is a lancet device according to the sixteenth or seventeenth invention in which the lancet has a second fitting portion formed of the cap portion for covering a tip of the puncture needle and the puncture body, in order to hold the puncture body in the case portion before use, and the third fitting portion has a fitting force stronger than that of the second fitting portion.

In such a structure, the fitting force of the third fitting portion which holds the puncture body and the puncture body holder when the lancet is loaded to the main body portion is stronger than the second fitting portion which holds the cap of the puncture body and the case portion.

Thus, when the lancet is used after it is loaded to the main body portion, the second fitting portion with weaker fitting force is disengaged before the third fitting portion. As a result, it becomes possible to prevent disengagement of the puncture holder and the puncture body when the cap is removed.

The lancet device according to the nineteenth invention is a lancet device according to any one of the sixteenth through eighteenth inventions in which the third fitting portion includes a groove portion and a protrusion. The groove portion is formed on an outer peripheral surface of the puncture body which is substantially parallel to the puncturing direction. The protrusion is formed on the puncture body holder of the main body portion, and fits to the groove portion.

In such a structure, since the protrusion formed on the puncture body holder fit to the groove portion formed on the outer peripheral surface of the puncture body, the third fitting portion can be readily formed.

The lancet device according to the twentieth invention is a lancet device according to the nineteenth invention in which the protrusion is formed on a tip of the puncture body holder via an elastic member having elasticity in a direction orthogonal to the puncturing direction.

In such a structure, for connecting the puncture body and the puncture holder, the protrusion formed on the puncture body holder resiliently deform in a direction orthogonal to the puncturing direction and fits to the groove portion formed on the puncture body.

By fitting the puncture body and the puncture holder utilizing elastic deformation, they can be readily fitted.

The lancet device according to the twenty-first invention is a lancet device according to the nineteenth or twentieth invention in which the puncture body further includes an insertion portion which is formed adjacent to the groove portion on a side connected to the main body portion and becomes narrower toward the side connected to the main body portion.

In such a structure, the insertion portion which becomes narrower toward the side connected to the main body portion is formed adjacent to the groove portion of the puncture holder, which fits the puncture body holder of the main body portion, on the side connected to the main body portion. This means that the puncture body includes the insertion portion and the groove portion in this order from the end on the side connected to the main body portion.

Thus, since the end of the puncture body on the side connected to the puncture body holder is narrow, the protrusion of the puncture body holder can be smoothly moved to the groove portion and fitted.

The lancet device according to the twenty-second invention is a lancet device according to any one of sixteenth through twenty first inventions further including a fitting release mechanism for releasing fitting at the third fitting portion.

In such a structure, fitting at the third fitting portion can be readily released by the fitting release mechanism for discarding the lancet.

The lancet according to the twenty-third invention is a lancet according to the first invention in which the first fitting portion is formed of a plurality of elastic members which are provided on an outer peripheral portion of the puncture body and resiliently deform in a direction orthogonal to a puncturing direction and a recessed portion which is formed on an inner periphery of the case portion and to which the elastic members fit.

In such a structure, the elastic members which are provided on the puncture body side and the recessed portion (opening) which is formed of the case portion side are combined to form the first fitting portion for holding the puncture body in the case portion after use.

Thus, by causing a part of the main body portion side to contact the elastic members provided on the outer peripheral portion of the puncture body in a process of moving the puncture body in the puncturing direction, for example, the elastic members can resiliently deform in the direction orthogonal to the puncturing direction. Accordingly, the elastic members can be relatively easily fitted to the recessed portion of the case portion, and the puncture body can be held in the case portion after puncturing.

The lancet according to the twenty-fourth invention is a lancet of the twenty-third invention in which the first fitting portion also functions as a second fitting portion for holding the puncture body in the case portion before puncturing.

In such a structure, first fitting portion for holding the puncture body in the case portion after puncturing also functions as the second fitting portion for holding the puncture body in the case portion before puncturing.

The first fitting portion is formed by combining the elastic members which are provided on the puncture body side and the recessed portion (opening) which is formed of the case portion side as described above.

With such a structure, by causing a part of the case portion side to contact the elastic members provided on the outer peripheral portion of the puncture body in a process of moving the puncture body in the puncturing direction, for example, the elastic members can resiliently deform in the direction orthogonal to the puncturing direction. Accordingly, fitting before puncturing can readily disengage.

The lancet according to the twenty-fifth invention is a lancet according to the twenty-fourth invention in which, for attaching the puncture body to the main body portion, the elastic members contact a part of the main body portion and resiliently deform in the direction orthogonal to the puncturing direction, and the puncture body moves relatively to the case portion in the puncturing direction to disengage the elastic members and the recessed portion.

In such a structure, for attaching the lancet to the main body portion side before puncturing, the elastic members which is a part of the puncture body contact a part of the main body portion and resiliently deform in the direction orthogonal to the puncturing direction, and thus, the puncture body and the case portion before puncturing disengage.

In this way, the puncture body which has been held in the case portion before puncturing can smoothly enter to a state available for puncturing.

The lancet according to the twenty-sixth invention is a lancet according to any one of the twenty-third through twenty-fifth inventions in which, for removing the puncture body from the main body portion, the puncture body moves relatively to the case portion in the puncturing direction, and the elastic members contact a part of the case portion and resiliently deform in the direction orthogonal to the puncturing direction so that the elastic members and the recessed portion fit each other.

In such a structure, for removing the puncture body (lancet) from the main body portion side after puncturing, first, the puncture body is moved relatively to the case portion in the puncturing direction, and the elastic members contact a part of the case portion and resiliently deform in the direction orthogonal to the puncturing direction.

The puncturing direction includes both the forward direction for discharging the puncturing body forward, and a retraction direction for setting the puncture body to a state available for discharge.

With such a structure, the size of the elastic members in the direction orthogonal to the puncturing direction can be made small. Thus, the elastic members can be fitted to the recessed portion formed on the case portion again.

The lancet according to the twenty-seventh invention is a lancet of the first invention in which the first fitting portion is formed by combining a recessed portion formed between a plurality of elastic members which are provided on an outer peripheral portion of the puncture body and resiliently deform in a direction orthogonal to the puncturing direction and a collar portion formed on a tip of the puncture body, and a convex portion formed on an inner peripheral surface side of the case portion.

In such a structure, the first fitting portion for holding the puncture body in the case portion before and after use is formed by combining the recessed portion formed between the collar portion formed on the puncture body side and the elastic members, and a convex portion formed on the side of the case portion.

Thus, by causing a part of the main body portion side to contact the elastic members formed on the outer peripheral portion of the puncture body in a process of moving the puncture body in the puncturing direction, for example, the elastic members can resiliently deform in the direction orthogonal to the puncturing direction. Accordingly, the convex portion of the case portion side can be relatively easily fitted to the recessed portion of the elastic member side, and the puncture body can be held in the case portion after puncturing.

The lancet according to the twenty-eighth invention is a lancet according to any one of the twenty-third through twenty seventh inventions in which the casing has a wall portion provided so as to cover the elastic members of the puncture body.

In such a structure, the wall portion located so as to cover the elastic members of the puncture body is provided on the casing side in order to prevent unintended deformation of the elastic member of the puncture body side which forms the fitting portion with the puncture body in the casing.

Thus, it becomes possible to prevent disengagement of the puncture body in the casing caused by erroneous contact to the elastic members from outside when the lancet is being packed in a box for transportation, after puncturing, or the like.

The lancet according to the twenty-ninth invention is a lancet according to the first invention in which the first fitting portion is formed of an elastic member formed in the case portion and resiliently deforms in a direction orthogonal to the puncturing direction, and a recessed portion formed on an outer peripheral portion of the puncture body.

In such a structure, the first fitting portion for holding the puncture body in the case portion after use is formed by combining the elastic member formed on the case portion side, and the recessed portion formed on the puncture body side.

Thus, since the elastic member of the main body portion side runs on the tapered portion or the like located near the recessed portion formed in a part of the puncturing body and resiliently deforms in a process of moving the puncture body in the puncture direction, the elastic member of the case portion can be relatively easily fitted to the recessed portion of the puncture body side to hold the puncture body in the case portion after puncturing.

The lancet according to the thirtieth invention is a lancet according to the twenty-ninth invention in which a cross section of the puncture body along the direction orthogonal to the puncturing direction has a circular shape.

In such a structure, the puncture body is formed such that the cross-section along the direction orthogonal to the puncturing direction has a circular shape.

Even when the puncture body with a cross-section of a circular shape is used, the elastic member formed in the case portion resiliently deforms in the direction orthogonal to the puncturing direction, and thus, two members can be relatively easily fitted to each other. As a result, a high accuracy in dimensions is not required for the puncture body, and the production yield of the puncture body improves in order to reduce the cost.

The lancet according to thirty-first invention is a lancet according to the twenty-ninth or thirtieth invention in which the puncture body further includes a tapered portion located so as to be adjacent to the recessed portion.

In such a structure, the tapered portion is formed at a position adjacent to the recessed portion to which the elastic member of the case portion fits.

Thus, for fitting the elastic member to the recessed portion, the elastic member resiliently deforms in the direction orthogonal to the puncturing direction as it runs on the tapered portion, and the two members can be readily fitted to each other.

Effects of the Invention

According to a lancet of the first invention, problems such that a user injures oneself by a puncture needle erroneously protruded from a tip of a puncture body when the lancet is discarded can be averted.

According to a lancet of the second invention, the puncture body can be held so as not to move in a puncturing direction in a case before use, and thus, security before use can be secured.

According to a lancet of the third invention, the puncture body held in the puncturing direction can be released at the same time as a cap is separated from a tip of the puncture body for use.

According to a lancet of the fourth invention, the number of components can be decreased in order to reduce the cost.

According to a lancet of the fifth invention, the puncture needle can be securely prevented from protruding out of the tip of the case after use, and a lancet with high safety after use which is secured more efficiently can be provided.

According to a lancet of the sixth invention, the puncture body can be readily held with a first fitting portion.

According to a lancet of the seventh invention, the first fitting portion can be readily formed.

According to a lancet of the eighth invention, the first fitting portion with a structure easy to be fitted and difficult to disengage can be formed.

According to a lancet of the ninth invention, a narrow side of a tapered shape is inserted first, and thus, the fitting portion, which is difficult to disengage once it is fitted, can be formed.

According to a lancet of the tenth invention, the fitting portion which is easy to be fitted but difficult to disengage can be formed.

According to a lancet of the eleventh invention, the fitting portion which is easy to be fitted but difficult to disengage can be formed.

According to a lancet of the twelfth invention, the puncture body is held at a few points, and thus, the fitting portion which is easy to be fitted and difficult to disengage can be formed.

According to a lancet of the thirteenth invention, the fitting portion which is easy to be fitted and difficult to disengage can be formed.

According to a lancet of the fourteenth invention, the fitting portion which fits at two points in the case portion can be formed.

According to a lancet of the fifteenth invention, body fluid collected from a puncture wound formed by the lancet is detected and a blood glucose concentration can be measured in such a state.

According to a lancet device of the sixteenth invention, a lancet device with high safety, particularly after use, can be provided.

According to a lancet device of the seventeenth invention, a lancet device with higher safety can be provided.

According to a lancet device of the eighteenth invention, fitting between the puncture holder and the puncture body can be prevented from disengaging when the cap is removed.

According to a lancet device of the nineteenth invention, a third fitting portion can be readily formed.

According to a lancet device of the twentieth invention, two members can be readily fitted.

According to a lancet device of the twenty-first invention, an end of the puncture body on the side connected to the puncture body holder is narrow, and a protrusion of the puncture holder can be smoothly moved and fitted to a groove portion of the puncture holder.

According to a lancet device of the twenty-second invention, the third fitting portion can be readily disengaged for discarding the lancet.

According to a lancet of the twenty-third invention, elastic members can be relatively readily fitted to a recess portion of the case portion to hold the puncture body in the case portion after puncturing.

According to a lancet of the twenty-fourth invention, elastic member resiliently deforms in a direction orthogonal to the puncturing direction, and fitting can be readily disengaged before puncturing.

According to a lancet of the twenty-fifth invention, the puncture body held in the case portion before puncturing can smoothly enter a state available for puncturing.

According to a lancet of the twenty-sixth invention, the elastic member can be fitted to the recessed portion formed on the case portion again.

According to a lancet of the twenty-seventh invention, the convex portion of the case portion side can be relatively easily fitted to the recessed portion on the elastic member side to hold the puncture body in the case portion after puncturing.

According to a lancet of the twenty-eighth invention, disengagement of the fitting holding the puncture body in the casing, which may be caused by erroneous contact to the elastic member from the outside during when the lancets are being packed in the box for transportation, after puncturing, or the like, can be prevented.

According to a lancet of the twenty-ninth invention, the elastic member of the case portion can be relatively easily fitted to the recessed portion of the puncture body side, and the puncture body can be held in the case portion after puncturing.

According to a lancet of the thirtieth invention, there is no need to require high accuracy in dimensions of the puncture body, and thus, the production yield of the puncture body is improved in order to reduce the cost.

According to a lancet of the thirty-first invention, for fitting the elastic member to the recessed portion the elastic member resiliently deforms in the direction orthogonal to the puncturing direction as it runs on a tapered portion, and the two members can be readily fitted to each other.

BRIEF DESCRIPTION OF THE DRAWINGS

FIG. 18 is a perspective view showing a structure of a puncture body holder portion of a casing included in the lancet shown in FIG. 17A and the like.

DESCRIPTION OF THE REFERENCE SYMBOLS

Figure 1:
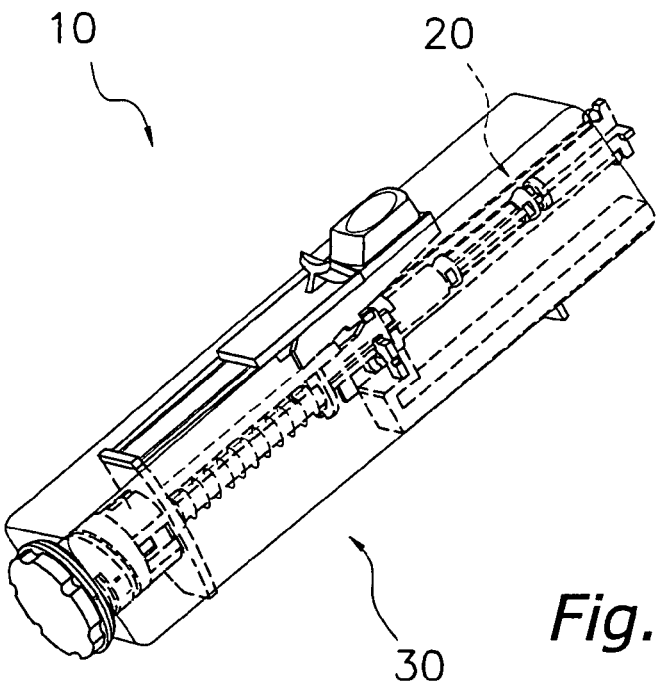
FIG. 1 is a perspective view showing an appearance of a lancet device according to one embodiment of the present invention.

10 lancet device
20 lancet
21 puncture needle
22 casing (case portion)

22a tubular portion
22b convex portion (first fitting portion)
22c groove (groove portion, second fitting portion)
22d first tapered portion
22e second tapered portion
23 puncture body
23a tapered portion
23b flange portion
23c groove (groove portion, first fitting portion)
23d insertion portion (connection portion)
23e groove (third fitting portion)
23g rib (protrusion, first fitting portion)
23h flange portion
24 cap (cap portion)
24a convex portion (second fitting portion)
24b lid
24c hole
30 main body (main body portion)
31 coil spring (biasing member)
32 puncture body holder
32a convex portion (protrusion, third fitting portion)
32b elastic portion (elastic member)
33 rotary member
34 biasing force applying portion
35 housing
35a puncture opening
36 detachment portion (fitting release mechanism)
36a insertion portion
36b releasing portion
37 set release button
50 lancet
51 biosensor (analysis tool)
120 lancet
122 casing (case portion)
122a tubular portion (wall portion)
122b tip opening
122c fitting portion
122d opening (recessed portion, first and second fitting portion)
123 puncture body
123a elastic arm member (elastic member, first and second fitting portion)
123aa tip portion
123d insert portion (connected portion)
123e step
220 lancet
221 puncture needle
222 casing (case portion)
222a tubular portion (wall portion)
222b elastic member (first fitting portion)
222c groove (second fitting portion)
222d convex portion
223 puncture body
223a tapered portion
223b flange portion
223c groove (first fitting portion)
223d insertion portion
224 cap
224a cap (second fitting portion)

BEST MODE FOR CARRYING OUT THE INVENTION

Hereinafter, a lancet device including a lancet according to one embodiment of the present invention will be described with reference to FIGS. 1 through 10B.

[Entire Structure of a Lancet Device 10]

A lancet device 10 according to one embodiment of the present invention is a device used for collecting body fluid when a diabetic patient measures a blood glucose level or the like. When in use, a puncture needle 21 (see FIG. 4) is protruded from an opening formed on a tip portion thereof with the tip portion abutting the skin to form a puncture wound.

Figure 2:
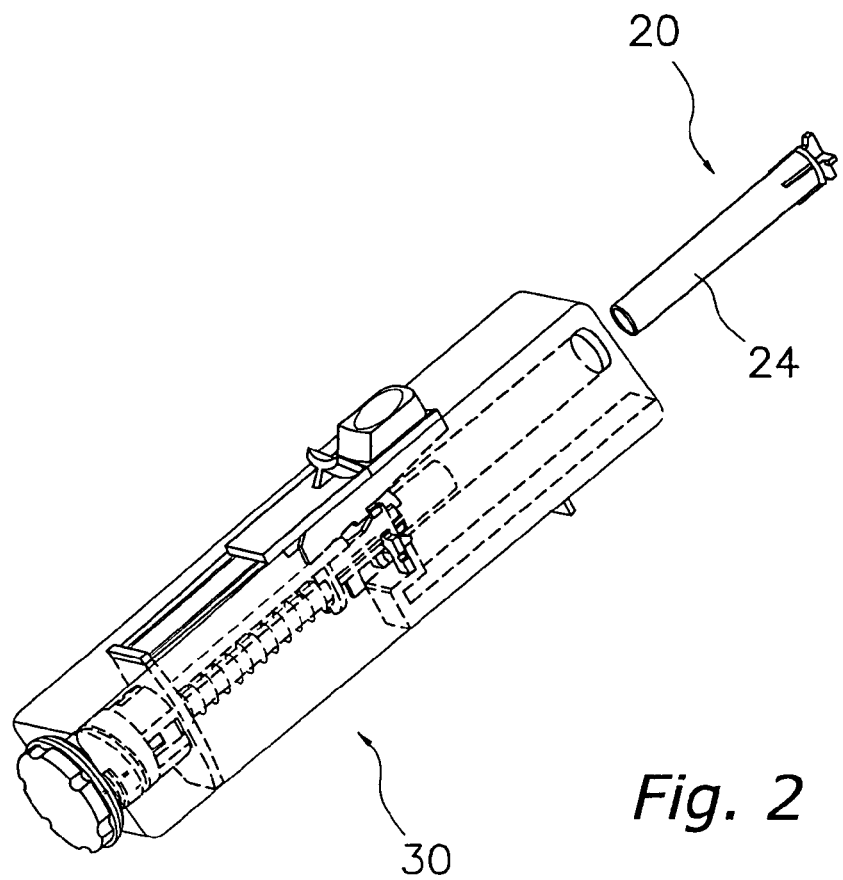
FIG. 2 is a perspective view showing a lancet and a main body which form the lancet device of FIG. 1.

Specifically, as shown in FIGS. 1 and 2, the lancet device 10 includes a lancet 20 and a main body 30.

The lancet 20 includes the puncture needle 21 (see FIG. 4) for forming a puncture wound which is made of stainless steel. As shown in FIG. 2, the lancet 20 is attached from a front end side of the main body 30.

The main body 30 includes a coil spring 31 (see FIG. 6) for applying a biasing force to the puncture needle 21 (see FIG. 4) such that it protrudes toward a predetermined direction for puncturing, and a return spring (not shown) for retracting the puncture needle 21 which is discharged by the coil spring 31 back into a housing 35.

Hereinafter, the term "front end side" refers to a side from which the tip of the puncture needle 21 of the lancet 20, which will be described later, protrudes, and the term "rear end side" refers to the opposite side.

[Structure of the Lancet 20]

Figure 3:
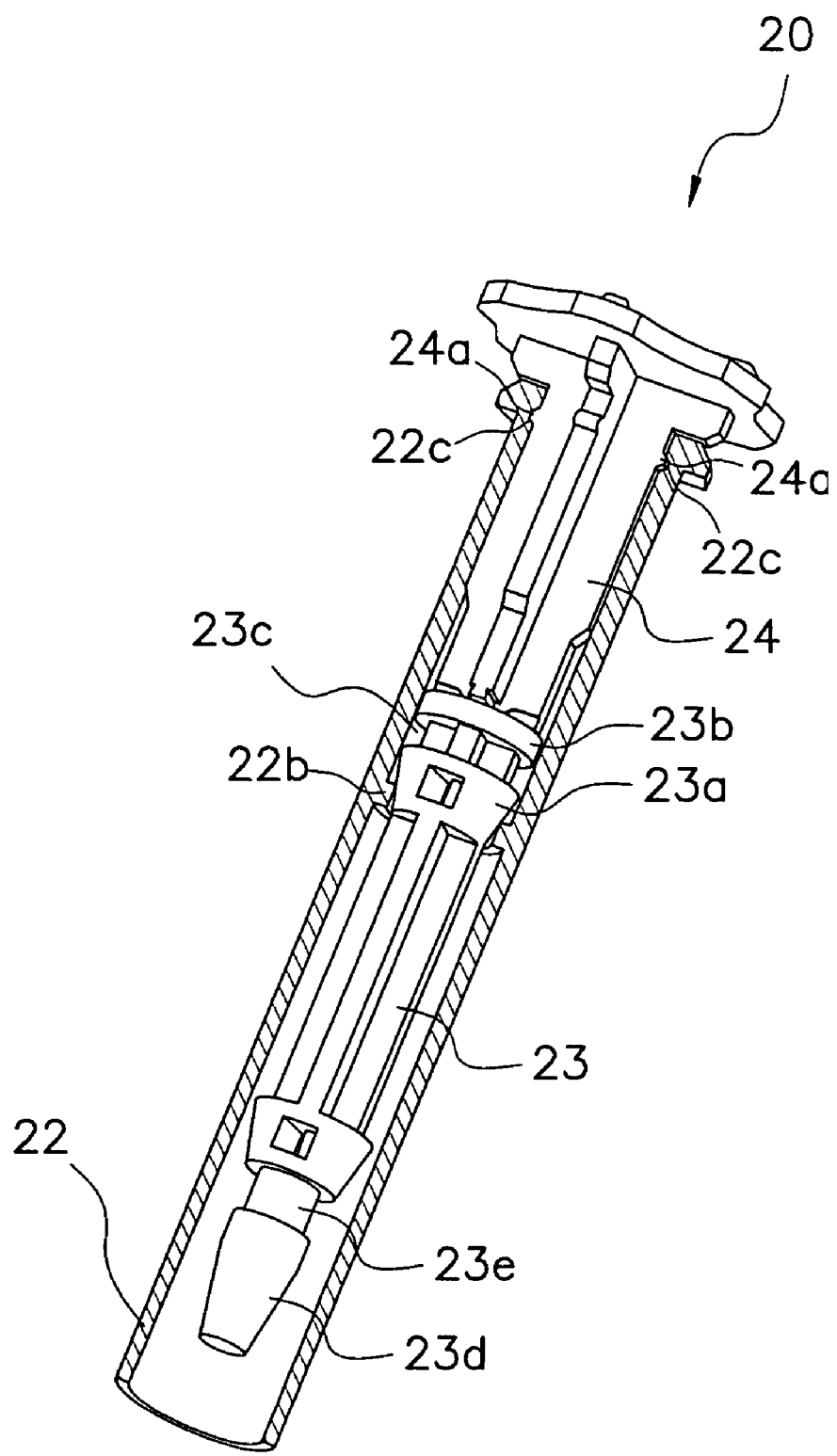
FIG. 3 is partially sectional view showing a structure inside a casing of the lancet included in the lancet device of FIG. 1.

As shown in FIG. 3, the lancet 20 includes a casing 22 which has a substantially cylindrical shape, and a puncture body 23 which is accommodated so as to be movable along the puncturing direction toward the front end side and the rear end side within the casing 22 when the lancet device 10 is being used. In FIG. 3, a cross section of the casing 22 is shown for the sake of convenience for describing the inner structure of the casing 22 which has a substantially cylindrical shape.

Figure 4:
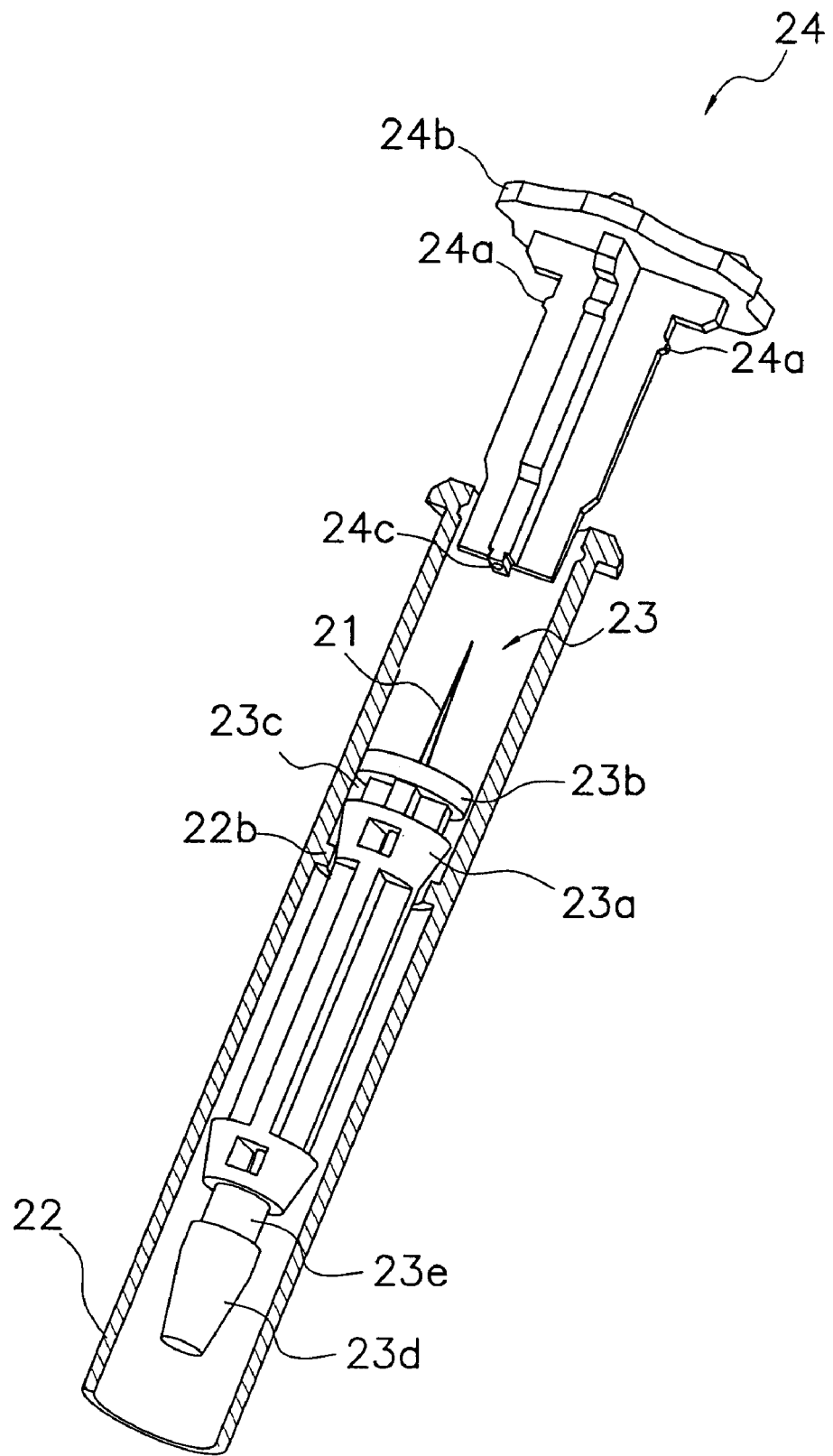
FIG. 4 is a perspective view of a puncture body and a cap included in the lancet of FIG. 2.

The puncture body 23 is formed of a resin integrally with the puncture needle 21 for forming a puncture wound on a skin (see FIG. 4). A resin molded part of the puncture body 23 includes a tapered portion 23a, a flange portion 23b, a groove 23c, an insertion portion 23d, and a groove 23e. The tapered portion 23a, the flange portion 23b, and the groove 23c are formed on the front end side from which the puncture needle 21 protrudes.

Figure 9A:
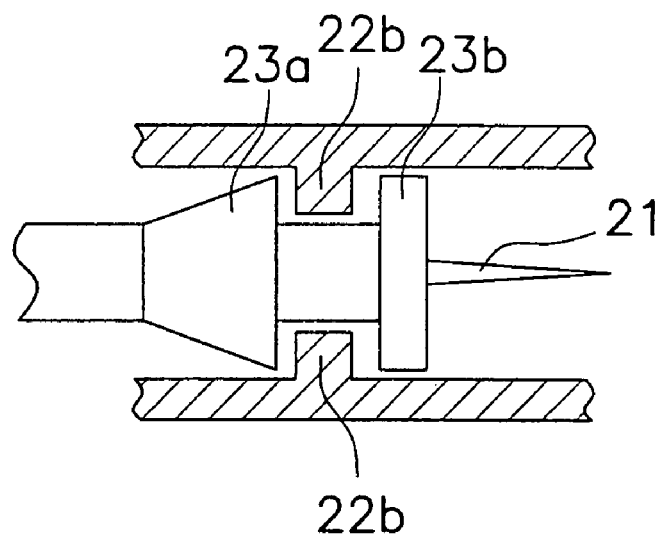
FIG. 9A is a sectional side elevation showing fitting between the puncture body and the casing of FIG. 8.
Figure 9B:
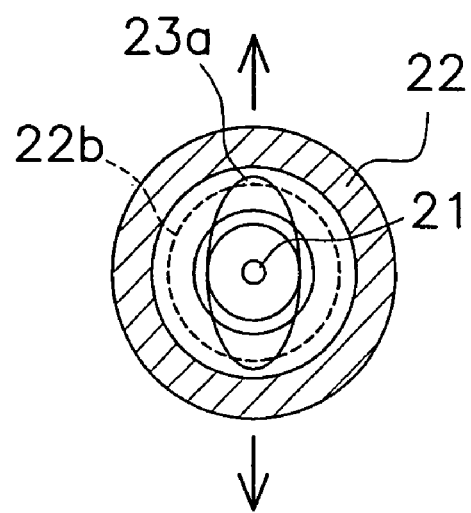
FIG. 9B is a sectional elevation thereof.

The tapered portion 23a is a member having a width which becomes narrower toward the rear end side. As shown in FIGS. 9A and 9B, a cross section of the tapered portion 23a orthogonal to the puncturing direction has an elliptical shape. The tapered portion 23a has a tilted angle preset to be between 5 and 30 degrees with respect to the puncturing direction. The lower limit (5 degrees) is defined because, if the tilt angle is smaller than this limit, the dimension of the puncture body 23 in a longitudinal direction becomes large, and the position where the puncture body 23 and the casing 22 fit each other may largely vary depending upon dimensional errors in a radial direction. On the other hand, the upper limit (30 degrees) is defined because, if the tilt angle is larger than this value, energy required for fitting the puncture body 23 to the casing 22 becomes large and the usability is deteriorated.

The flange portion 23b is a disc-like member which is formed on the tip of the front end side of the puncture body 23. The puncture needle 21 protrudes from the center of the disc.

The groove 23c is a recess formed between the tapered portion 23a and the flange portion 23b. After use, the puncture body 23 is moved toward the rear end side relatively to the casing 22. A convex portion 22b of the casing 22, which will be described below, is fitted to the groove 23c so that the puncture body 23 can be held within the casing 22 (see FIG. 8).

The insertion portion 23d is inserted into a puncture body holder 32 of the main body 30, which will be described below.

Figure 7A:
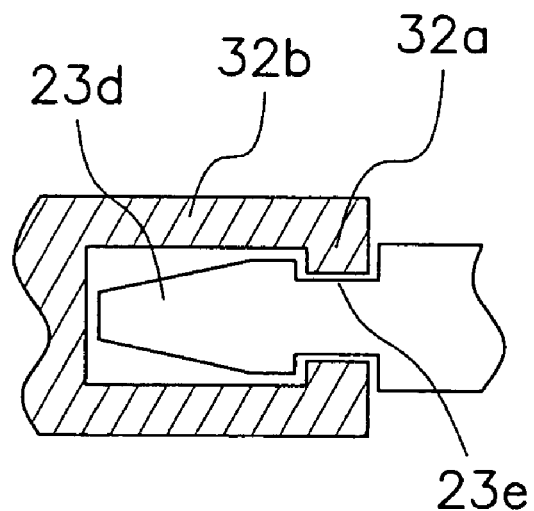
FIGS. 7A and 7B are sectional side elevations showing fitting between the puncture body and a puncture body holder.

A tip portion of the puncture body holder 32 resiliently deforms and a convex portion 32a formed on the tip fits to the groove 23e (see FIG. 7A). In this way, an elastic force of the coil spring 31 which is located at the rear end side of the puncture body holder 32 in the main body 30 can move and retract the puncture body 23 in the puncturing direction together with the puncture body holder 32.

As shown in FIGS. 3 and 4, a cap 24 is attached to the puncture needle 21 so as to cover the tip portion. Thus, a point of needle of the puncture needle 21 is not exposed before use. The cap 24 is integrally formed with the puncture needle 21 similarly to the puncture body 23, and a part of the cap 24 is connected to the flange portion 23b of the puncture body 23. For use, the cap 24 is screwed and pulled such that the connected portion between the cap 24 and the flange portion 23b is cut and the puncture needle 21 is exposed within the casing 22 as shown in FIG. 4. The cap 24 includes a protrusion 24a, a lid 24b and a hole 24c. The protrusion 24a is a portion protruding toward a direction orthogonal to the puncturing direction. As shown in FIG. 3, when the cap 24a is being attached to the casing 22, the protrusion 24a fits to a groove 22c formed on an end of the front end side of the casing 22, which will be described below. In this way, the puncture body 23 before use can be held within the casing 22. The lid 24b serves as a lid which covers the tip of the casing 22 before use. The hole 24c is a hole which is formed when the puncture needle 21, the puncture body 23 and the cap 24 are integrally formed so as to adhere closely to the front end side of the puncture needle 21. The puncture needle 21 is inserted into the hole 24c until the cap 24 is separated from the puncture body 23.

Figure 5:
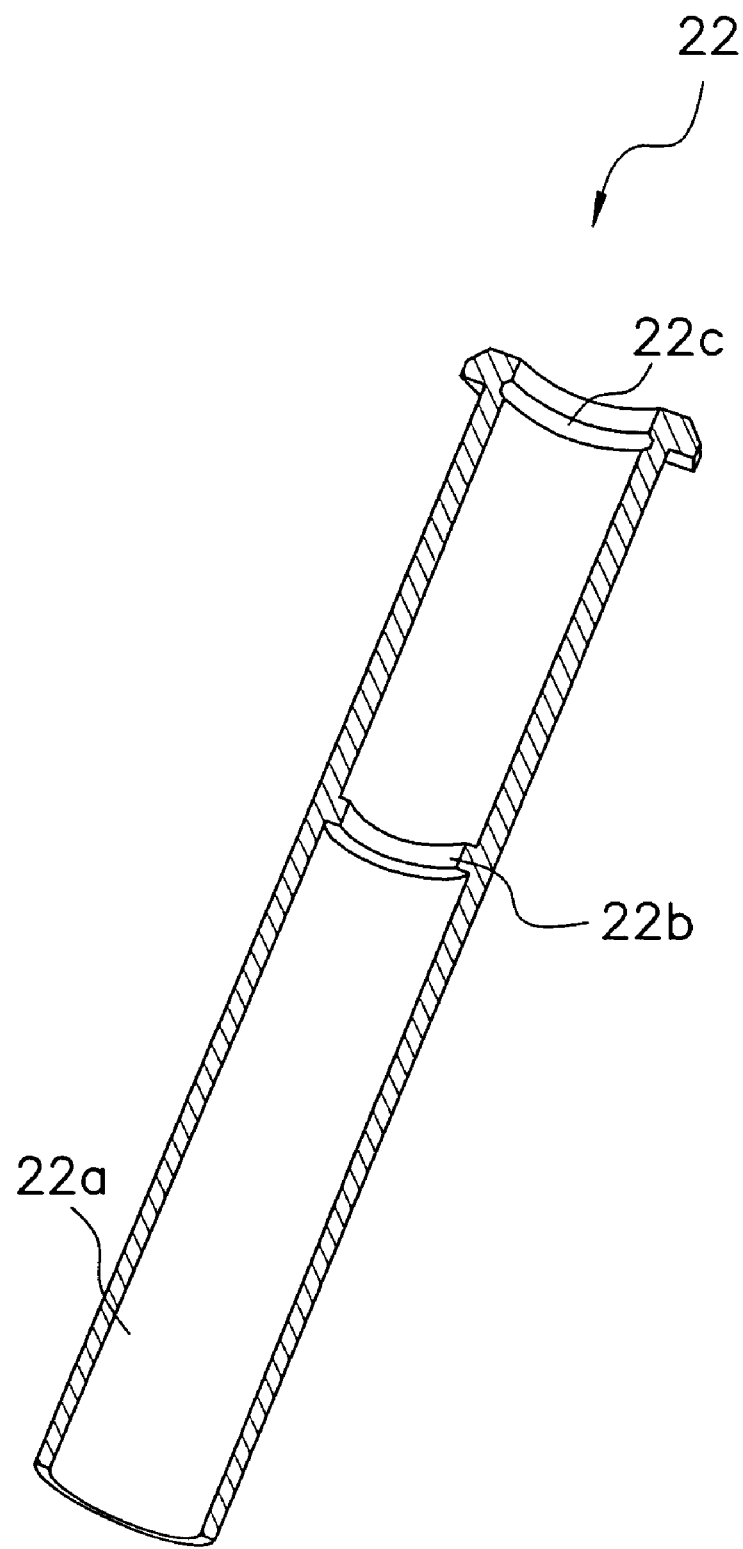
FIG. 5 is a cross sectional view of a structure inside the casing included in the lancet of FIG. 1.
Figure 8:
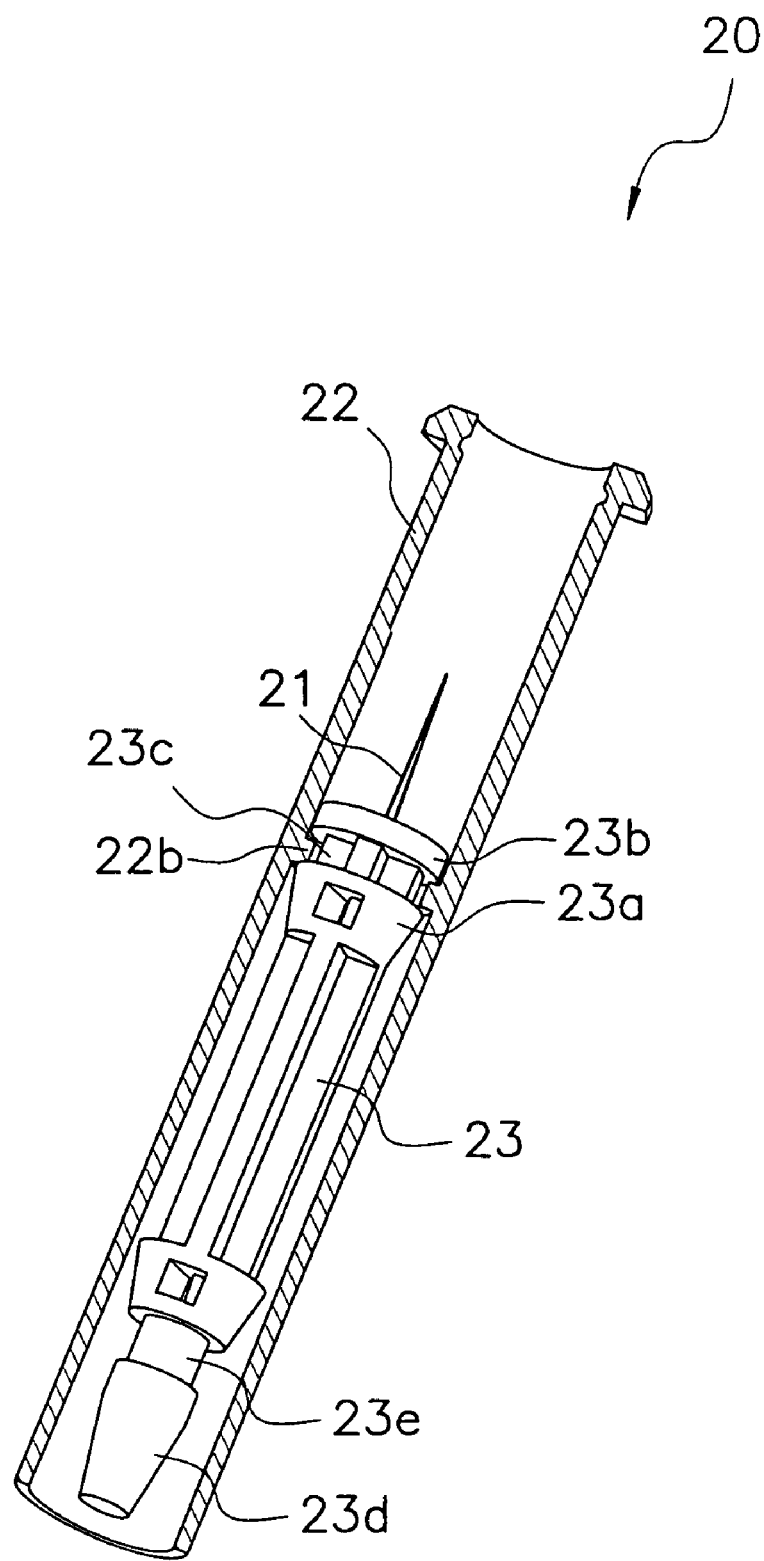
FIG. 8 is partially sectional view showing a state where the puncture body is held in the casing when the lancet is removed from the main body after use.

The casing 22 is a member having a substantially cylindrical shape. The puncture body 23 is accommodated within the casing 22 from since when it has not been used yet until the time it is discarded after use. As shown in FIG. 5, the casing 22 has an inner peripheral surface 22a, a convex portion 22b, and a groove 22c. The inner peripheral surface 22a is formed to have a radius slightly larger than those of the tapered portion 23a, the flange portion 23b and the like of the puncture body 23. When in use, the puncture body 23 moves along the puncturing direction toward the front end side or the rear end side. The convex portion 22b is a member protruding from the inner peripheral surface 22a of the casing 22 toward inside, and is formed near the center in a longitudinal direction of the casing 22. For discarding the lancet 20 after use, the puncture body 23 is retracted toward the rear end side, and the groove 23c is fitted to the convex portion 22b as shown in FIG. 8. In this way, the puncture needle 21 can be prevented from protruding out of the tip of the casing 22 after use. Accordingly, safety after use can be secured. The groove 22c is a recess formed on the inner peripheral surface 22a of the casing 22 on the front end side of the casing 22. Before use, the protrusion 24a of the cap 24 is fitted into the groove 22c. Thus, the puncture body 23 can be held within the casing 22 such that it does not move in the puncturing direction toward the front end side or the rear end side.

[Structure of the Main Body 30]

Figure 6:
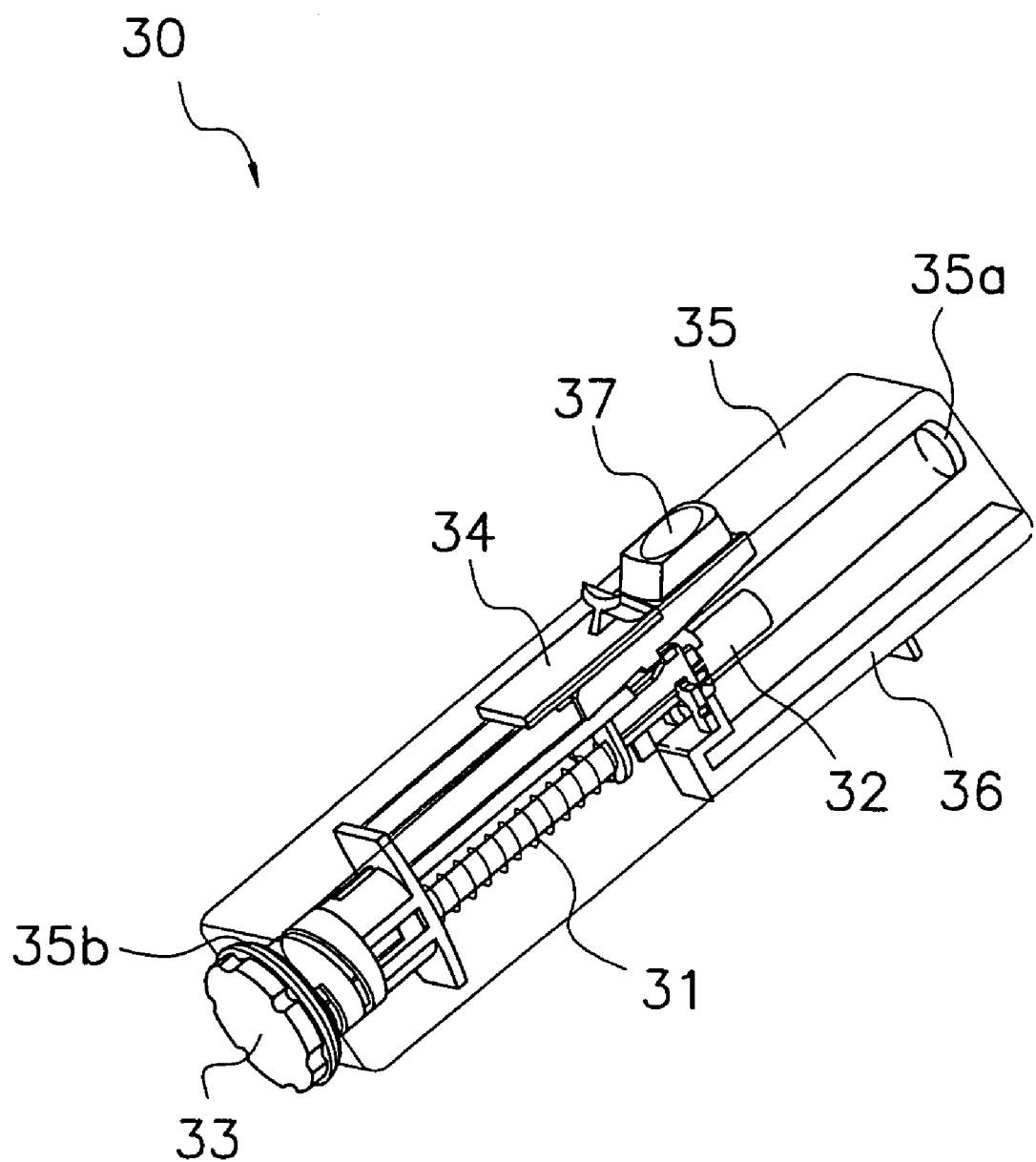
FIG. 6 is a perspective diagram showing a structure of the main body included in the lancet device of FIG. 1.

As shown in FIG. 6, the main body 30 includes the coil spring 31, the puncture body holder 32, a rotary member 33, a biasing force applying portion 34, a transparent housing 35, a detachment portion (fitting release mechanism) 36, and a set release button 37. The lancet 20 described above is attached from the front end side of the main body 30 (see FIG. 2).

The coil spring 31 is a member for applying a biasing force for advancing the puncture body 23 of the lancet 20 toward the puncturing direction. The coil spring 31 is placed on the rear end side of the puncture body holder 32.

The puncture body holder 32 holds a portion on the rear end side of the puncture body 23 (the insertion portion 23d and the groove 23e) that is inserted from a puncture opening 35a formed on the tip of the housing 35. The puncture body holder 32 has a convex portion (protrusion) 32a which fits to the groove 23e of the puncture body 23 on an end of the front end side. When the insertion portion 23d of the puncture body 23 is inserted, a portion around the convex portion 32a resiliently deforms, and the convex portion 32a fits to the groove 23e formed on the rear end side of the puncture body 23 (see FIG. 7A). The convex portion 32a of the puncture body holder 32 and the groove 23e on the rear end side of the puncture body 23 fit to each other with a fitting force stronger than that between the protrusion 24a of the cap 24 and the groove 22c of the casing 22 as described above. Thus, when the cap 24 is removed while the lancet 20 is being attached to the main body 30, the cap 24 and the casing 22 is disengaged faster than the puncture body holder 32 and the puncture body 23 is disengaged because the force of fitting is smaller. As a result, even when the cap 24 is pulled out toward the front end side in order to wrench off the cap 24 from the casing 22, the puncture body 23 and the puncture body holder 32 remain fitted to each other while the cap 24 is removed from the casing 22. The rotary member 33 is rotated in a circumferential direction with an axial direction being a center by rotating an exposed dial portion. The rotary member 33 has a rib formed to have a helical pattern on an inner surface of a tubular portion on the front end side of the dial portion. When the puncture body holder 32 is moved toward the front end side by an elastic force of the spring, a convex portion formed on the rear end side of the puncture body holder 32, which is not shown, abuts the rib and an amount of movement is restricted. By rotating the rotary member 33, a position where the convex portion and the rib abut can be changed, and thus, an amount of movement of the puncture body holder 32 can be adjusted. Accordingly, the position of the puncture body 23 in the puncturing direction can be adjusted back and forth. It becomes possible to adjust amount of protrusion of the puncture needle 21 and control a depth of puncturing by rotating the rotary member 33 before puncturing skin.

The biasing force applying portion 34 is a member which compresses the coil spring 31 and discharges the puncture body 23 for discharging the puncture body 23 in the puncturing direction. The biasing force applying portion 34 is exposed from a side surface of the housing 35.

The housing 35 includes the coil spring 31, the puncture body holder 32, and the like as described above, and forms an outer casing of the lancet device 10. The housing 35 includes a puncture opening 35a on an end of the front end side and an opening 35b in which the rotary member 33 is accommodated on an end of the rear end side. The puncture opening 35a is where the lancet 20 is inserted, and a tip of the puncture needle 21 comes out for puncturing. The opening 35b is formed into a circular shape so as to conform to the shape of the rotary member 33.

Figure 12:
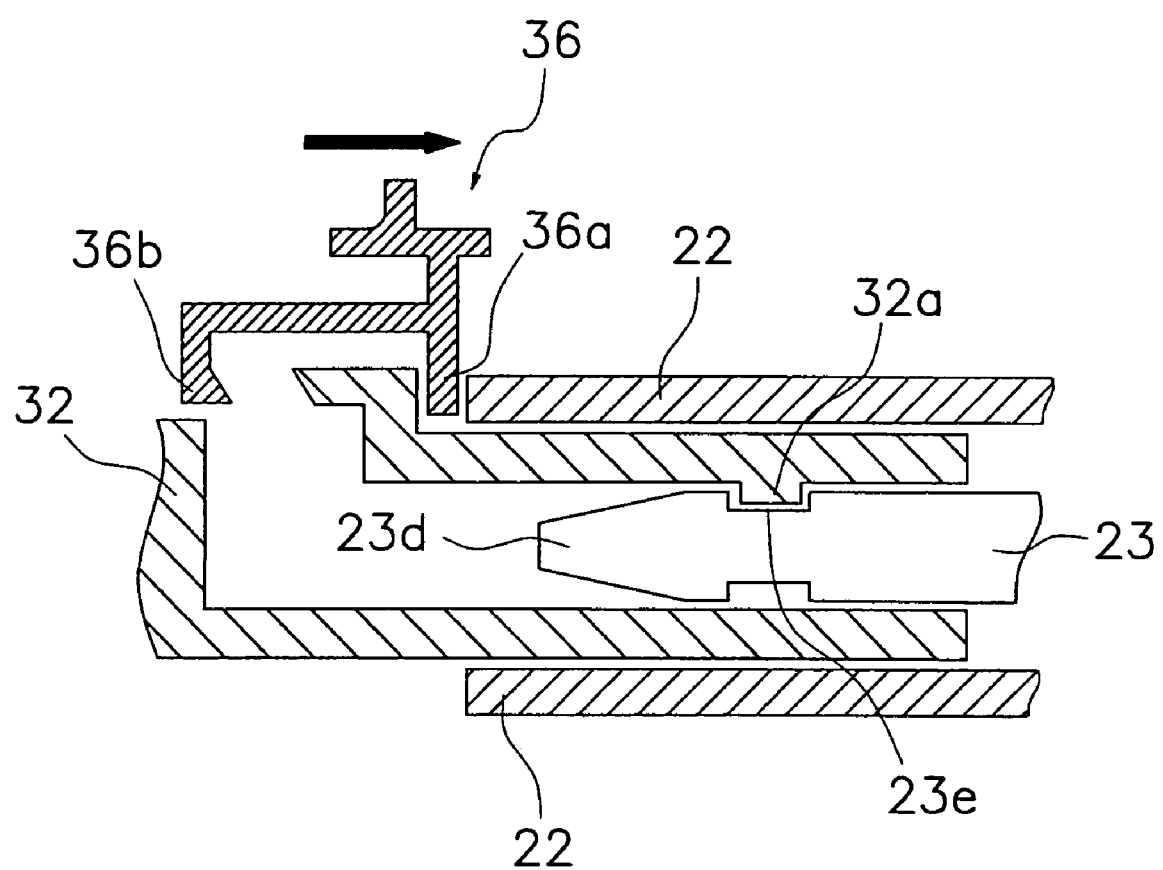
FIG. 12 is a sectional side elevation illustrating a fitting release mechanism for disengaging fitting which forms a first fitting portion.

The detachment portion 36 is exposed from a surface opposite to the surface from which the biasing force applying portion 34 is exposed in the housing 35 having a substantially rectangular parallelepiped shape. The detachment portion 36 is positioned so as to contact an end of the casing 22 on the rear end side in the housing 35. After puncturing is finished, as shown in FIG. 12, the detachment portion 36 is moved toward the front end side. First, only the casing 22 abutting the insertion portion 36a moves forward toward the front end side (see an arrow in the figure). Thus, the convex portion 22b of the casing 22 fits to the groove 23c of the puncture body 23. Then, when the detachment portion 36 is further moved forward, a releasing portion 36b which is a part of the detachment portion 36 pushes a portion of the convex portion 32a of the puncture body holder 32 up. Thus, the puncture body 23 (the insertion portion 23d and the groove 23e) which has been held is released, and the lancet 20 is removed from the main body 30.

More specifically, at a step before removing the lancet 20 from the main body 30, the casing 22 of the lancet 20 is pushed toward the front end side before the puncture body 23 is pushed. This means that the puncture body 23 moves toward the rear end side relatively to the casing 22. Inside the lancet 20, the tapered portion 23a formed around the center of the puncture body 23 run on the convex portion 22b formed on the inner peripheral surface 22a of the casing 22. The portion around convex portion 22b formed on the inner peripheral surface 22a of the casing 22 resiliently deforms and the tapered portion 23a further moves toward the rear end side. The puncture body 23 stops and is held in the casing 22 when the convex portion 22b fits into the groove 23c of the puncture body 23. Since the rear end side of the tapered portion 23a is narrower, the puncture body 23 can be smoothly moved to the position where it fits.

The convex portion 22b of the casing 22 and the groove 23c of the puncture body 23 fit to each other after puncturing before the fitting between the groove 23e of the puncture body 23 on the rear end side and the convex portion 32a of the puncture body holder 32 is released as described above. The fitting force between convex portion 22b and the groove 23c is stronger than that between the groove 23e on the rear end side and the convex portion 32a. This force is so strong that once they are fitted it is difficult to release. Thus, for detaching the lancet 20 from the main body 30, fitting with weaker fitting force (fitting between the convex portion 32a of the puncture body holder 32 and the groove 23e of the puncture body 23) is released first among two sets of fitted members in order to allowing detachment of the lancet 20 from the main body 30. Further, with the groove 23c of the puncture body 23 being fitted to the convex portion 22b of the casing 22, the tip of the puncture needle 21 of the puncture body 23 is not exposed from the end of the casing 22 on the front end side. Thus, possible danger that the tip of the puncture needle 21 after puncturing comes out from the tip of the casing 22 after the lancet 20 is removed from the main body 30 and a user is injured or be infected with a disease by body fluid attached to the tip of the used puncture needle 21 can be averted. Moreover, the lancet 20 once removed from the main body 30 and the puncture body 23 fit to each other such that the puncture body 23 is held in the casing 22. Thus, reuse of the lancet 20 is more difficult than conventional lancets.

[Descriptions on Operations of the Lancet Device 10]

For starting use of the lancet device 10 according to the present embodiment, first, a new unused lancet 20 is inserted into the puncture opening 35a of the main body 30 (see FIG. 6) as shown in FIG. 2. As the lancet 20 is inserted to the inner part of the puncture opening 35a, the insertion portion 23d formed on the end of the puncture body 23 on the rear end side shown in FIG. 3 passes by the convex portion 32a of the puncture body holder 32 and is inserted to the inner part. Then, as shown in FIG. 7A, the groove 23e formed adjacent to the insertion portion 23d fits to the convex portion 32a of the puncture body holder 32. In this way, the lancet 20 is loaded to the main body 30 completely, and the lancet 20 is cocked. The puncture needle 21 is prepared for discharge.

Next, as shown in FIG. 4, the cap 24 integrally formed with the puncture body 23 is removed for exposing the puncture needle 21. Since a part of the cap 24 is connected a surface of the flange portion 23b of the puncture body 23 on the front end side, the cap 24 is rotated such that the connected portion is wrenched off, and the cap 24 is removed. A force is applied to the cap 24 to be removed in a direction to pull it toward the front end side. Thus, the puncture body 23 partially connected to the cap 24 is also affected by the force pulling it toward the front end. However, as shown in FIG. 7 when the cap 24 is removed, the end of the puncture body 23 on the rear end side is held by the puncture body holder 32. The force of fitting the puncture body 23 and the puncture body holder 32 is stronger than the force of fitting between the cap 24 and the casing 22, and a force necessary for removing the cap 24 from the puncture body 23. As a result, even when the cap 24 is removed from the casing 22, the puncture body 23 is not pulled out with the cap 24 and is held in the casing 22. As described above, by separately providing the fitting position of the puncture body 23 (cap 24) to the casing 22 before the puncturing, and the fitting position to the casing 22 after puncturing (when being discarded), the puncturing operation can be performed smoothly compared to the case where the puncture body 23 is held by being fitted at only one position in the casing 22.

For discharging the once punctured puncture body 23 again, the biasing force applying portion 34 cocks and the coil spring 31 is compressed to apply the biasing force. In such a state, cocking may be released by the biasing force release button 37.

Next, the set release button 37 is pressed to release setting with the puncture opening 35a being abut on the skin to be punctured. The tip of the puncture needle 21 protrudes from the puncture opening 35a formed on the tip of the front end side of the main body 30 by a predetermined amount. Then, immediately after puncturing, the puncture needle 21 returns to the casing 22 by a spring force of the return spring, which is not shown. A range of movement of the puncture needle 21 before and after puncturing is from a standby position of the puncture body 23 before the discharge as shown in FIG. 4 and a puncturing position at which the tip of the puncture needle 21 is protruded by a few millimeters.

After puncturing, the lancet 20 is removed from the main body 30 by the detachment portion 36 and discarded. The lancet 20 is removed from the main body 30 by the detachment portion 36 as shown in FIG. 6. Specifically, the detachment portion 36 is moved toward the front end side to release the puncture body 23 which has been held by the puncture body holder 32, and the lancet 20 can be removed from the puncture opening 35a. More specifically, as the detachment portion 36 is moved toward the front end side, only the casing 22 moves toward the front end side first. Thus, the puncture body 23 held by the puncture body holder 32 moves toward the rear end side relatively to the casing 22. At this time, the tapered portion 23a formed around the center of the puncture body 23 pushes and expands the portion of the convex portion 22b formed on the inner peripheral surface 22a of the casing 22 as it moves. Then, the convex portion 22b of the casing 22 fits to the groove 23c of the puncture body 23. A force of this fitting is strong such that the tip portion of the puncture needle 21 can be prevented from protruding from the front end side of the casing 22 after the lancet 20 is removed from the main body 30. In this way, protrusion of the puncture needle 21 can be prevented by the cap 24 before use, and, after use, by holding the puncture body 23 in the casing 22 with fitting of a strong force. Thus, a danger can be averted both before and after use.

After the convex portion 22b of the casing 22 fits to the groove 23c of the puncture body 23, the puncture body 23 which has been held by the puncture body holder 32 as shown in FIG. 7A is released. Specifically, since the force of fitting between the convex portion 22b and the groove 23c is stronger than that between the convex portion 32a of the puncture body holder 32 and the groove 23e of the puncture body 23, the puncture body 23 which has been held by the puncture body holder 32 is released first. The fitting between the convex portion 22b and the groove 23c of the puncture body 23 in the casing 22 may be made easy to fit and difficult to be disengaged by utilizing the shape of the tapered portion 23a, elastic deformation of the convex portion 22b or the inner peripheral surface 22a, and the like as described above.

With the above-described procedure, the used lancet 20 is removed from the main body 30, and discarded. In the removed lancet 20, the puncture body 23 is held within the casing 22 by a strong fitting force. Thus, it is ensured a user injuring oneself by the tip of the puncture needle 21 which comes out from the tip of the casing 22 or being infected with a disease by body fluid attached to the tip of the puncture needle 21 can be prevented. Further, the lancet 20 once removed from the main body 30 and the puncture body 23 fit to each other such that the puncture body 23 is held in the casing 22. Thus, reuse of the lancet 20 is more difficult than conventional lancets.

[Features of the Lancet Device 10]

(1)

As shown in FIG. 3, the lancet 20 included in the lancet device 10 of the present embodiment includes the casing 22, and the puncture body 23 accommodated in the casing 22 so as to be movable in the puncturing direction. Further, convex portion 22b is formed on the inner peripheral surface 22a of the casing 22, and a recessed portion (the groove 23c) is formed on the puncture body 23. They form fitting such that the puncture body 23 is held in the casing 22 so as to be immovable in the puncturing direction for removing the lancet 20 from the main body 30.

Such a structure allows the puncture body 23 to be held in the casing 22 so as to be immovable in the puncturing direction as shown in FIG. 8 after the lancet 20 is being removed from the main body 30. In this state, the puncture body 23 is held at a position where the tip of the puncture needle 21 does not protrude from the end of the casing 22 on the front end side. Thus, possible danger that a user is injured when the user discard the lancet 20 or be infected with a disease by body fluid attached to the tip of the puncture needle 21 can be securely averted unlike the conventional lancets in which caps are attached to tips of the lancets after use or protrusion of puncture needles is suppressed by simple fitting. Moreover, the lancet 20 once removed from the main body 30 and the puncture body 23 fit to each other such that the puncture body 23 is held in the casing 22. Thus, reuse of the lancet 20 is more difficult than conventional lancets.

(2)

In the lancet 20 of the present embodiment, as shown in FIG. 8, the groove 23c of the puncture body 23 and the convex portion 22b of the casing 22 form a first fitting portion for holding the puncture body 23 in the casing 22 after the lancet 20 is removed from the main body 30. The groove 23c and the convex portion 22b have a fitting force so strong that once they are fitted it is difficult to disengage.

With such a structure, movement of the puncture body 23 along the puncturing direction in the casing 22 is prohibited in the used lancet 20. Thus, it becomes possible to surely avert a danger of injury of a user or infection to a disease, which may be caused by the puncture needle 21 protruding out from the tip of the lancet 20 when the used lancet 20 is being discarded after puncturing or the like.

(3)

In the lancet 20 of the present embodiment, the first fitting portion is formed by combining the groove 23c and the convex portion 22b as shown in FIGS. 9A and 9B in order to fit the puncture body 23 and the casing 22 after use. The puncture body 23 has the tapered portion 23a formed adjacent to the groove 23c. A cross section of the tapered portion 23a which is orthogonal to the puncturing direction has an ellipsoidal shape. Thus, the puncture body 23 is held with the tapered portion 23a being in contact with the convex portion 22b, which is formed on the inner peripheral surface 22a of the casing 22 and has a circular shape, at two points.

By using the tapered portion 23a having a cross section of an ellipsoidal shape for fitting within the casing 22, the fitting can be readily achieved with the inner peripheral surface 22a of the casing 22 resiliently deforming.

(4)

In the lancet 20 of the present embodiment, the first fitting portion (the groove 23c and the convex portion 22b) which prohibits the movement of the puncture body 23 in the puncturing direction in the casing 22 holds the puncture body 23 at a position closer to the rear end side than the position where the puncture body 23 stands by for discharge in the puncturing direction. This means that, in the lancet 20, the tapered portion 23a of the puncture body 23 moves freely in a part closer to the front end side than the convex portion 22b formed on the inner peripheral surface 22a of the casing 22 for puncturing from the time before use to the time it is being used and perform puncturing. When puncturing is finished and the lancet 20 is removed from the main body 30, the puncture body 23 is moved toward the rear end side relatively to the casing 22. Thus, the groove 23c of the puncture body 23 fits to the convex portion 22b, and the puncture body 23 is held so as to be immovable in the puncturing direction.

With such a structure, the lancet 20 which can secure the safety after use can be provided.

(5)

In the lancet 20 of the present embodiment, as shown in FIG. 8, the first fitting portion which prohibits movement of the puncture body 23 in the puncturing direction in the casing 22 after use is formed of the groove 23c formed on the puncture body 23 and the convex portion 22b formed on the inner peripheral surface 22a of the casing 22.

With such a structure, the first fitting portion with a strong fitting force can be readily formed even with a simple structure of combining one set of a recessed portion and a convex portion.

(6)

In the lancet 20 of the present embodiment, as shown in FIG. 8, a portion around the convex portion 22b resiliently deforms when the convex portion 22b formed on the inner peripheral surface 22a of the casing 22 fits to the groove 23c of the puncture body 23.

By forming the first fitting portion by utilizing the elastic deformation, fitting which is easy to be fitted and difficult to disengage can be achieved.

(7)

In the lancet 20 of the present embodiment, as shown in FIG. 4, the puncture body 23 has the tapered portion 23a on the rear end side of the groove 23c of the puncture body 23 which forms the first fitting portion. The tapered portion 23a becomes narrower toward the rear end side.

By inserting the puncture body 23 toward the convex portion 22b formed on the inner peripheral surface 22a of the casing 22 from the narrow side of the tapered portion 23a, a strong fitting force which makes it easy to fit and difficult to disengage can be achieved.

(8)

In the lancet 20 of the present embodiment, as shown in FIG. 3, a second fitting portion for holding the puncture body 23 in the casing 22 before use is formed of the protrusion 24*a* formed on the cap 24 and the groove 22*c* formed on a tip of the front end side of the inner peripheral surface 22*a* of the casing 22.

With such a structure, the tip of the puncture needle 21 can be covered by the cap 24 before use, and the cap 24 covering the puncture needle 21 can be temporally tacked in the casing 22. For use, the cap 24 can be wrenched off and disconnected from the puncture body 23 so that the puncture body 23 can become available readily. Also, injury which may be caused by the puncture needle 21 before use can be prevented.

(9)

In the lancet 20 of the present embodiment, as shown in FIG. 3, the cap 24 for covering the puncture needle 21 so as not to expose the tip of the puncture needle 21 before use is integrally formed with the puncture body 23.

By forming the cap 24 integrally with the puncture body 23, the number of components can be decreased to reduce the cost.

(10)

The lancet device 10 of the present embodiment has, as shown in FIGS. 3 and 7A, a third fitting portion (the groove 23*e* and the convex portion 32*a*) for holding the puncture body 23 from the rear end side when the lancet 20 is attached to the main body 30.

With such a structure, the puncture body 23 can be discharged in the puncturing direction with the puncture body holder 32 by applying the biasing force to the puncture body holder 32 by the coil spring 31. Since the puncture body 23 is held so as not to disengage in the puncturing direction, the lancet device 10 with high safety can be achieved. Furthermore, after use, the third fitting portion is released and the first fitting portion (the groove 23*c* and the convex portion 22*b*) holds the puncture body 23 in the casing 22 to secure the safety after use.

(11)

In the lancet device 10 of the present embodiment, the fitting force of the third fitting portion (the groove 23*e* and the convex portion 32*a*) is weaker than that of the first fitting portion (the groove 23*c* and the convex portion 22*b*).

Thus, when the lancet 20 is removed from the main body 30 after use, the third fitting portion having a weaker fitting force is disengaged first. Therefore, it becomes possible to prevent that the first fitting portion disengages before the third fitting portion, and the puncture body 23 becomes movable within the casing 22 when the lancet 20 is removed from the main body 30.

(12)

In the lancet device 10 of the present embodiment, the fitting force of the third fitting portion (the groove 23*e* and the convex portion 32*a*) is stronger than that of the second fitting portion (the groove 22*c* and the protrusion 24*a*).

Thus, even when the cap 24 covering the tip of the lancet 20 is wrenched off to be detached from the puncture body 23 for use, the puncture body 23 can be firmly held in the puncture body holder 32 so that it does not disengage from the puncture body holder 32.

(13)

In the lancet device 10 of the present embodiment, as shown in FIGS. 3 and 7A, the third fitting portion is formed of the groove 23*e* formed on the puncture body 23 and the convex portion 32*a* formed on the tip portion of the puncture body holder 32.

In this way, such a structure, a necessary fitting force can be obtained between the puncture body 23 and the puncture body holder 32 and fitting which is easy to be fitted and difficult to be disengaged can be formed even with a simple structure.

(14)

In the lancet device 10 of the present embodiment, as shown in FIG. 7A, the convex portion 32*a* which forms the third fitting portion is formed on a tip of an elastic portion 32*b* which has elasticity in the direction orthogonal to the puncturing direction.

Since a part of the puncture body holder 32 resiliently deforms, the convex portion 32*a* formed on its tip can be readily fitted to the groove 23*e* on the rear end side of the puncture body 23.

(15)

In the lancet device 10 of the present embodiment, as shown in FIG. 3 and the like, the insertion portion 23*d* is provided on the end of the rear end side which is adjacent to the groove 23*e* formed on the puncture body 23 which forms the third fitting portion. The insertion portion 23*d* becomes narrower toward the rear end side.

Thus, the puncture body 23 can be inserted to the puncture body holder 32 from the narrow side of the insertion portion 23*d*, and the convex portion 32*a* can be readily fitted to the groove 23*e*. Accordingly, fitting which is easy to be fitted and difficult to disengage can be achieved.

(16)

In the lancet device 10 of the present embodiment, as shown in FIG. 12, the detachment portion 36 is advanced toward the front end side in the puncturing direction. Thus, the puncture body 23 and the puncture body holder 32 are disengaged with the puncture body 23 being held in the casing 22 to remove the puncture body 23 with the lancet 20 from the main body 30.

With such a structure, the lancet 20 can be readily discarded after use by only moving the detachment portion 36 forward. Further, in the lancet 20, the puncture body 23 is held in the casing 22, so the lancet 20 can be discarded with the safety after use being secured.

OTHER EMBODIMENTS

One embodiment of the present invention has been described above. However, the present invention is not limited to the above embodiment, and various modifications can be made without departing from the gist of the invention.

(A)

In the above embodiment, the structures of the fitting portions are respectively described. However, the structures of the fitting portions are not limited to those described in the above embodiment.

For example, a convex portion and a recessed portion may be switched. Alternatively, fitting utilizing elastic deformation of the members may be used instead of simple fitting utilizing combination of a convex portion and a recessed portion.

However, combining a convex portion and a recessed portion and also utilizing elastic deformation to form fitting as in the above embodiment is preferable since fitting which is easy to be fitted and difficult to disengage can be formed even with a simple structure.

(B)

In the above embodiment, as shown in FIGS. 9A and 9B, the groove 23*c* is formed on the puncture body 23 adjacent to the tapered portion 23*a* which has a cross section of an ellipsoidal shape and protrudes toward the long sides thereof. The convex portion 22b having a cross section of a circular shape is formed on the casing 22 along the inner periphery portion. The groove 23c and the convex portion 22b are fit to each other to form the first fitting portion in the example described above. However, the structure of the first fitting portion is not limited to this.

Figure 10A:
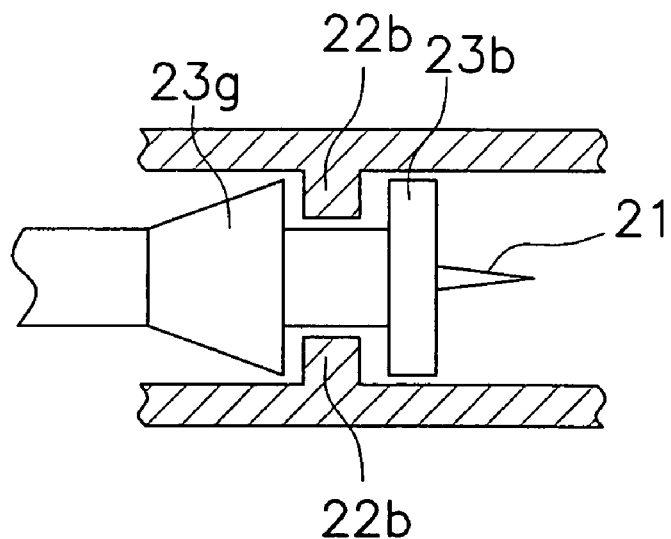
FIG. 10A is a sectional side elevation showing fitting between a puncture body and a casing according to another embodiment of the present invention.
Figure 10B:
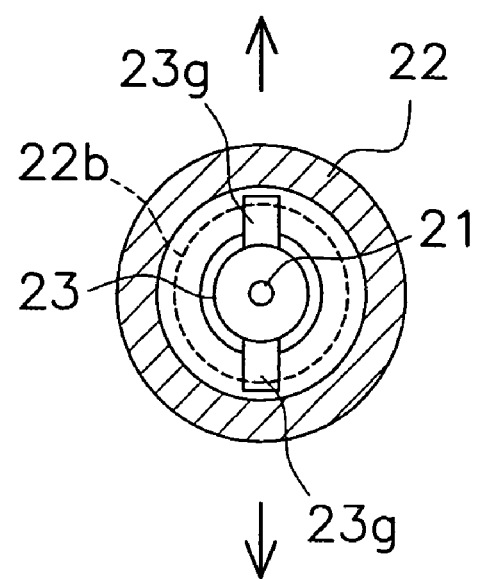
FIG. 10B is a sectional elevation thereof.

For example, as shown in FIGS. 10A and 10B, a plurality of ribs 23g having a cross section of a circular shape may be used. The ribs 23g may extend radially from the puncture body 23 and fit to the groove 22c formed on the inner periphery side of the casing 22. In such a structure, the puncture body 23 can be held at two points in the casing 22 as in the example where the long sides of the cross section of the ellipsoidal shape are used as protrusions.

(C)

In the above embodiment, it is described that fitting utilizing elastic deformation of the elastic portion 32b adjacent to the convex portion 32a as shown in FIG. 7A is used for the third fitting portion (the groove 23e and the convex portion 32a). However, the present invention is not limited to such an example.

Figure 7B:
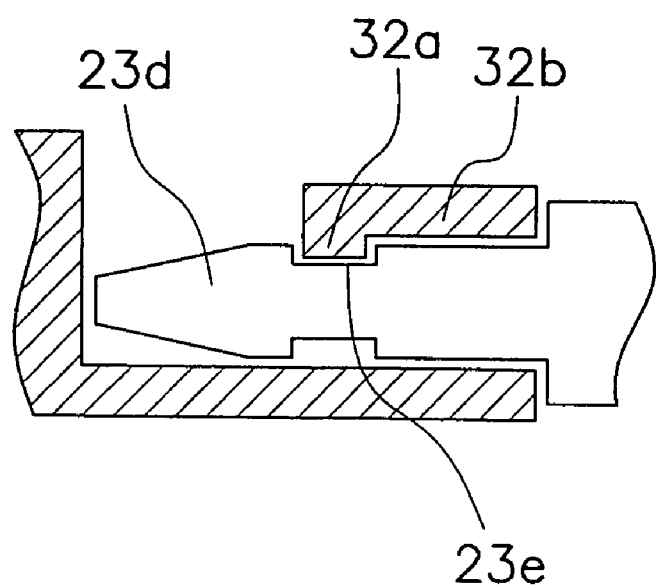

For example, as shown in FIG. 7B, the convex portion 32a formed on one side of the puncture body holder 32 may fit to the groove 23e by elastic deformation of the elastic portion 32b.

(D)

In the above embodiment, a spring force is used for a mechanism to discharge the puncture needle 21. However, the present invention is not limited to such an example.

For example, an electromagnetic force, or a force of air may be used as well as the spring force.

(E)

In the above embodiment, the tapered portion 23a is formed on the puncture body 23, and the convex portion 22b which fits to the groove 23c formed adjacent to the tapered portion 23a as mentioned above is formed on the inner surface of the tubular portion 22a of the casing 22. However, the present invention is not limited to such an example.

Figure 11A:
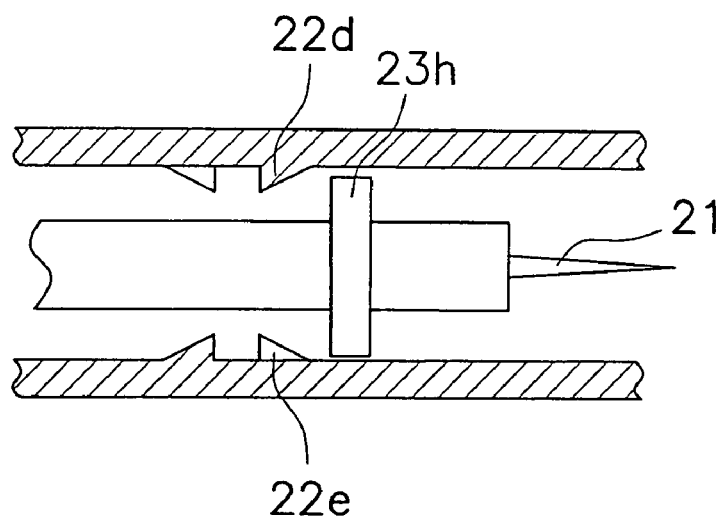
FIG. 11A is a sectional side elevation showing fitting between a puncture body and a casing according to still another embodiment of the present invention.
Figure 11B:
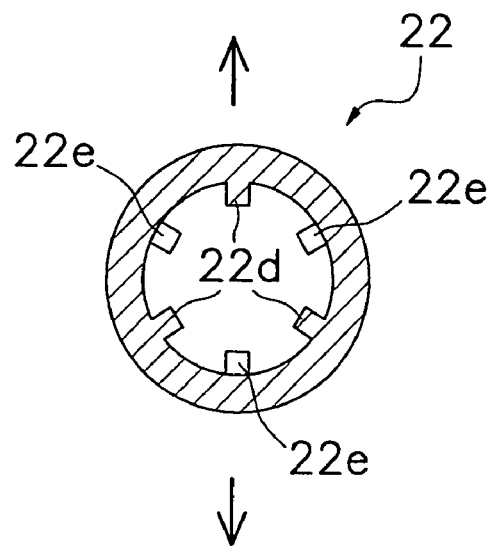
FIG. 11B is a cross sectional view showing a structure inside the casing.

For example, as shown in FIGS. 11A and 11B, a first tapered portion 22d and a second tapered portion 22e may be formed on the side of the tubular portion 22a of the casing 22 rather than on the puncture body 23 side. A flange portion 23h formed on the puncture body 23 may fit to a groove portion between the first tapered portion 22d and the second tapered portion 22e to form the first fitting portion.

(F)

In the above embodiment, the convex portions and recessed portions which form the fitting portions are respectively formed on the members which fit to each other. However, the present invention is not limited to such an example.

For example, the convex portions and the recessed portions may respectively be formed on the other member as described above.

(G)

In the above embodiment, the present invention is applied to the lancet 20 and the lancet device 10 for forming a puncture wound. However, the present invention is not limited to such an example.

Figure 13:
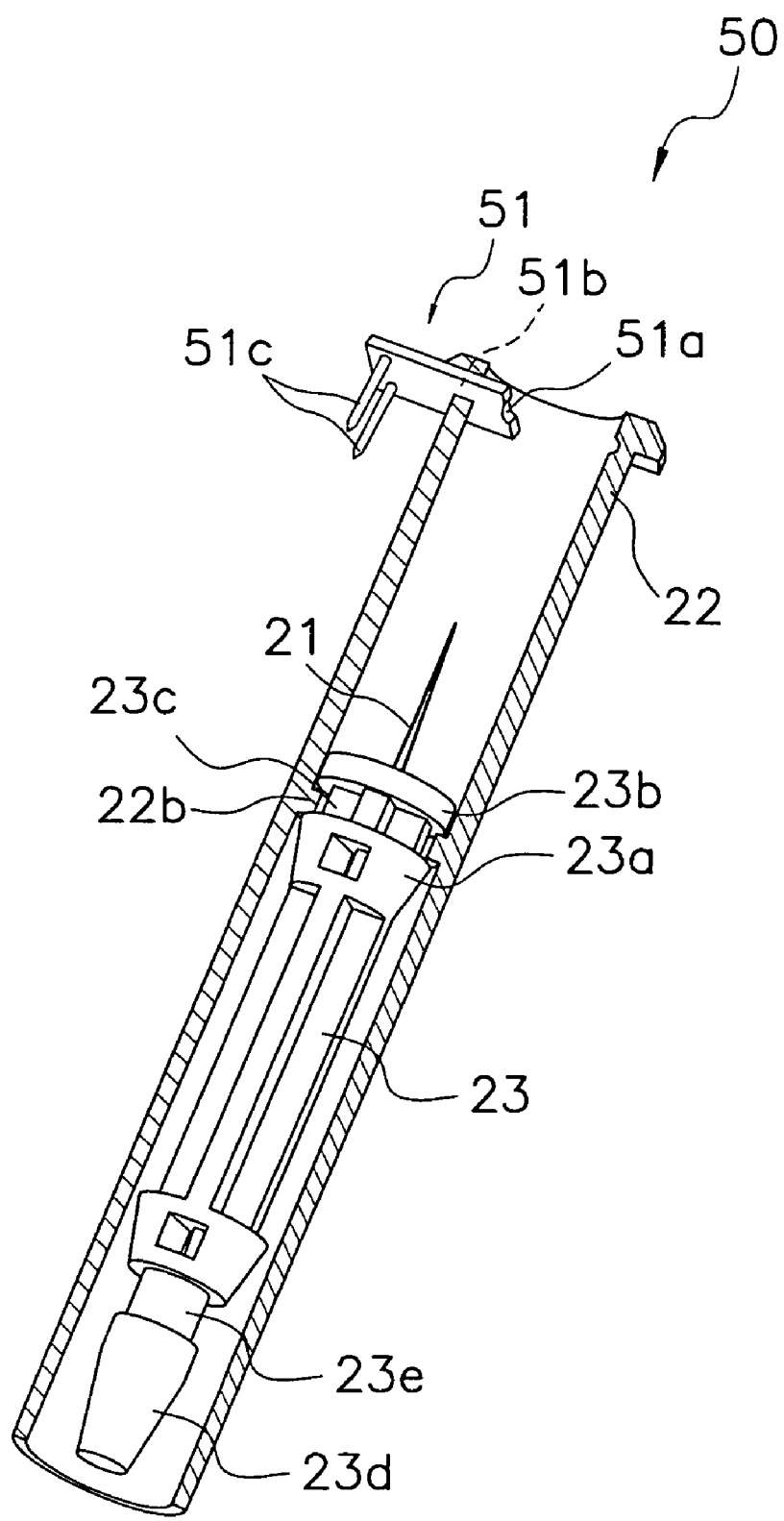
FIG. 13 is a partially sectional view showing a structure of a lancet according to still another embodiment of the present invention.

For example, as shown in FIG. 13, the present invention may be applied to a lancet 50 with a biosensor 51 for detecting blood flowing out from a puncture wound being attached to the end of the casing 22 on the front end side. The biosensor 52 collects blood flowing out from a puncture wound from an inlet 51a, and causes it to react with a reagent on a reagent portion 51b. Then, a measurement result at the biosensor 51 is sent to a measurement device, which is not shown, through a terminal 51c connected to the measurement device. With such a structure, a glucose concentration can be measured for blood attached to the biosensor 51 with the needle puncturing the skin.

(H)

In the above embodiment, fitting between the casing 22 and the puncture body 23 after puncturing is achieved by combining the first tapered portion 22d formed on the side of the inner peripheral surface of the casing 22 and the groove 23c formed on the outer peripheral surface of the puncture body 23. However, the present invention is not limited to such an example.

Figure 14:
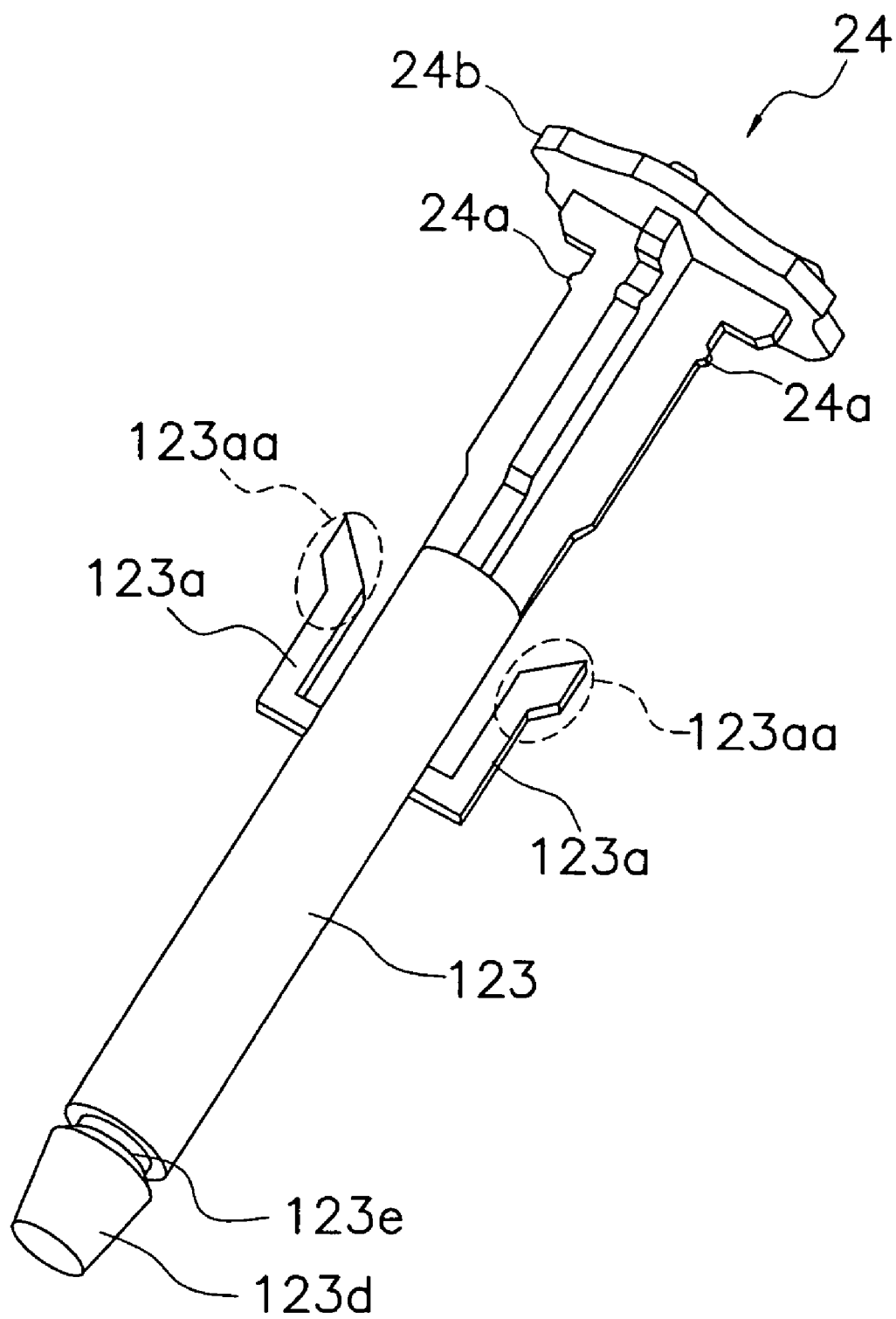
FIG. 14 is a perspective view showing a structure of a puncture body included in a lancet according to another embodiment of the present invention.
Figure 15A:
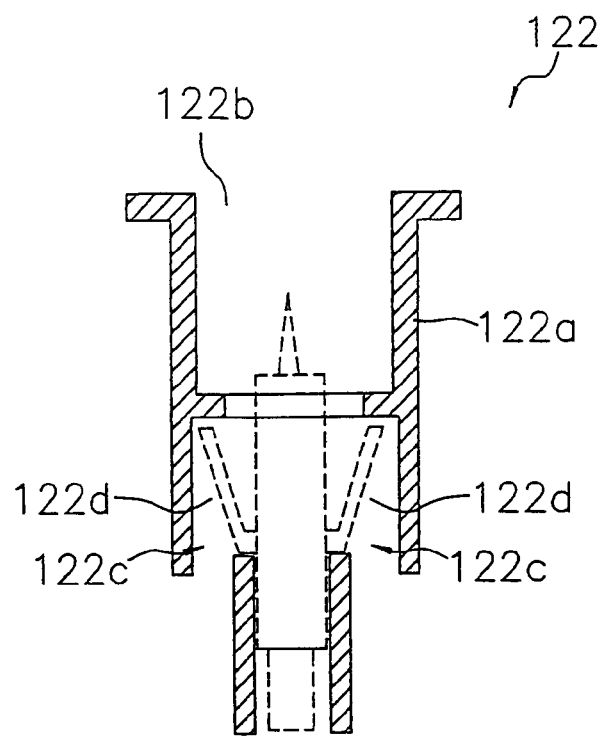
FIG. 15 is a perspective view showing a structure of a casing which forms the lancet with the puncture body of FIG. 14.
Figure 15B:
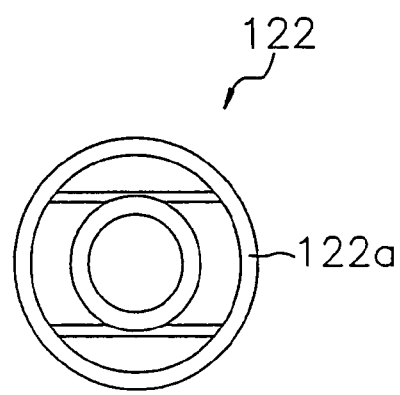

For example, the cap 24 and a puncture body 123 as shown in FIG. 14 and a casing (case portion) 122 as shown in FIG. 15 may be combined and a lancet 120 (the puncture body 123) and the casing 122 may be fitted. Specifically, elastic arm members (elastic members, the first and second fitting portion) 123a are formed symmetrically on both sides of the outer peripheral portion of the puncture body 123 shown in FIG. 14. Tip portions 123aa of the elastic arm members 123a are inserted from a tip opening 122b formed on an inner peripheral side of a tubular portion 122a of the casing 122 shown in FIG. 15, and fit to an opening (recessed portion, the first and the second fitting portion) 122d formed in a fitting portion 122c formed inside the tubular portion 122a. In this way, the puncture body 123 can be held within the casing 122 so as not to move. Further, it is also possible to prevent disengagement of fitting holding the puncture body 123 in the casing 122 which may be caused by erroneously contacting the elastic arm members 123a when they are being packed in a box for transportation or after puncturing.

Hereinafter, a specific way of fitting will be described with reference to FIGS. 16A through 16C.

Figure 16A:
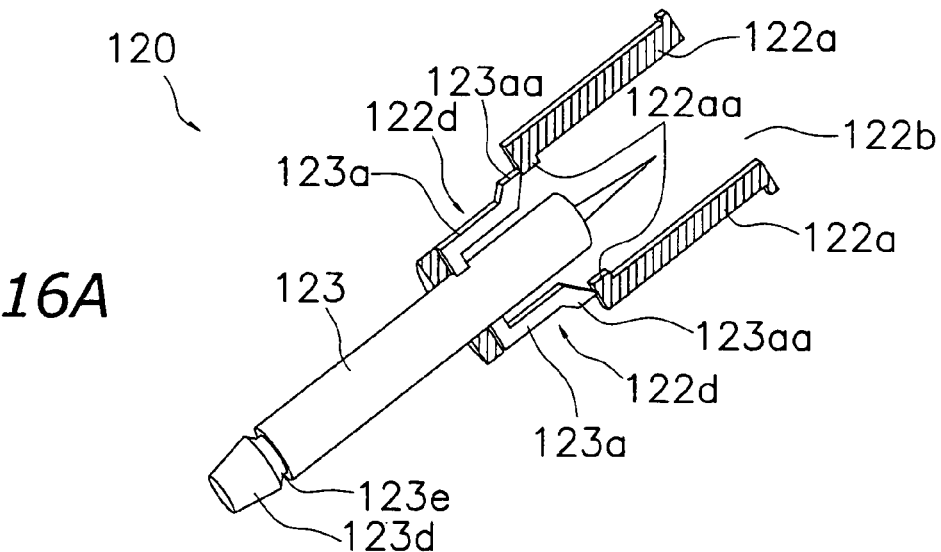
FIGS. 16A through 16C are perspective views showing the lancet including the puncture body and the casing respectively shown in FIGS. 14 and 15 before puncturing, during puncturing, and after puncturing.

First, as shown in FIG. 16A, the puncture body 123 is inserted from the side of the tip opening 122b of the casing 122 and is held with the elastic arm members 123a fitting to the opening 122d which is formed closer to the rear end than the main body portion 122a before use. At this state, the tip portions 123aa of the elastic arm members 123a are locked onto convex portion 122aa of the main body portion 122a, and the puncture body 123 becomes immovable in the puncturing direction.

Next, for loading the puncture body 123 to the main body part including the biasing force member, the puncture body 123 is inserted in the puncturing direction. A portion of the main body contacts the tip portions 123aa of the elastic arm members 123a, and the elastic arm members 123a are pressed toward the inner periphery and resiliently deform. Then, as shown in FIG. 16B, the fitting between the opening 122d of the casing 122 and the elastic arm members 123a of the puncture body 123 is released. When the puncture body 123 is further moved toward the front end side relatively to the casing 122 along the puncturing direction, the tip portions 123aa of the elastic arm members 123a moves closer to the front end side than the convex portion 122aa formed on the rear end of the main body portion 122a. In this way, the puncture body 123 becomes movable in the casing 122. Thus, the lancet holder on the main body part (not shown) with the insertion portion 123d of the puncture body 123 and a portion of a step 123e being fitted each other can be biased by the biasing member toward the front end in the direction of the puncturing for puncturing.

Figure 16B:
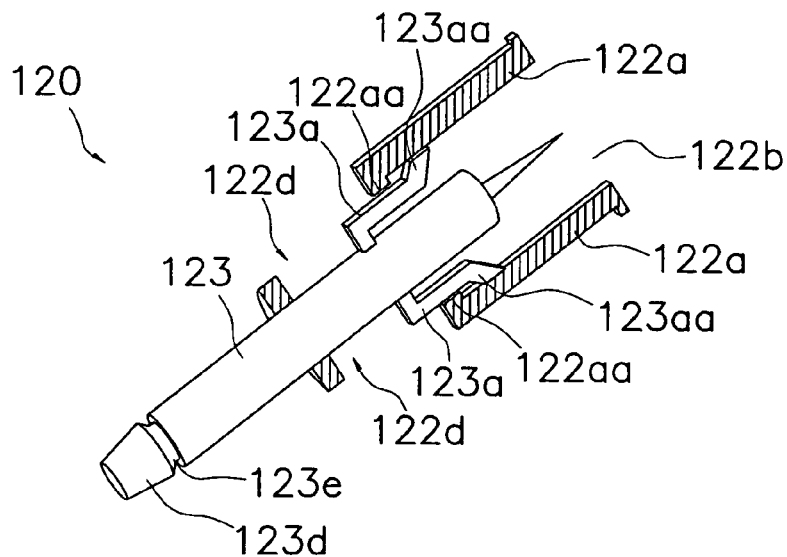
Figure 16C:
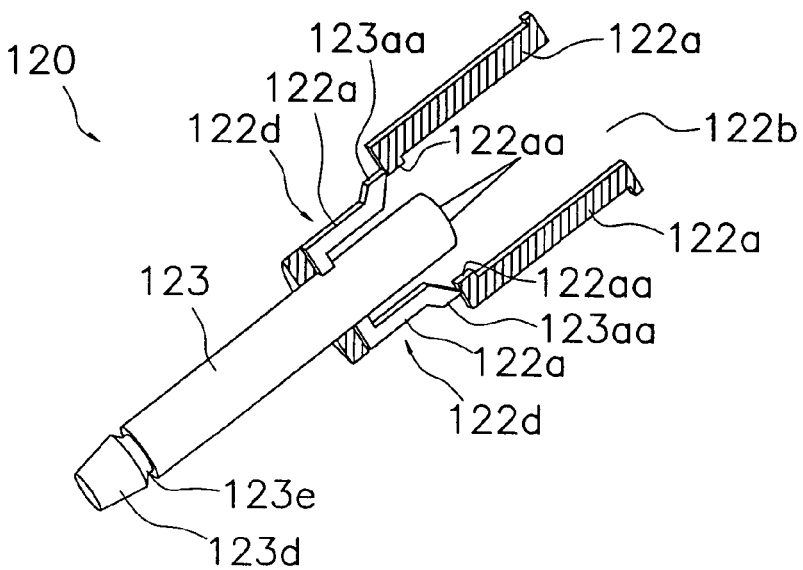

After puncturing, the puncture body 123 is moved toward to rear end in the puncturing direction relatively to the casing 122 from the state as shown in FIG. 16B. The tip portions 123aa of the elastic arm members 123a run on the convex portions 122aa of the main body portion 122a of the casing 122 and resiliently deform toward inner periphery side. Then, as shown in FIG. 16C, the elastic arm members 123a fit to the opening 122d of the casing 122. At this state, the tip portions 123aa of the elastic arm members 123a are locked onto convex portion 122aa on the rear end portion of the main body portion 122a of the casing 122, and the puncture body 123 becomes immovable in the puncturing direction in the casing 122.

As described above, by resiliently deforming the elastic arm members 123a of the puncture body 123 in a direction orthogonal to the puncturing direction, i.e., toward inner periphery side to fit and disengage to the opening 122d of the casing 122, the puncture body 123 can be readily held and released.

Figure 19:
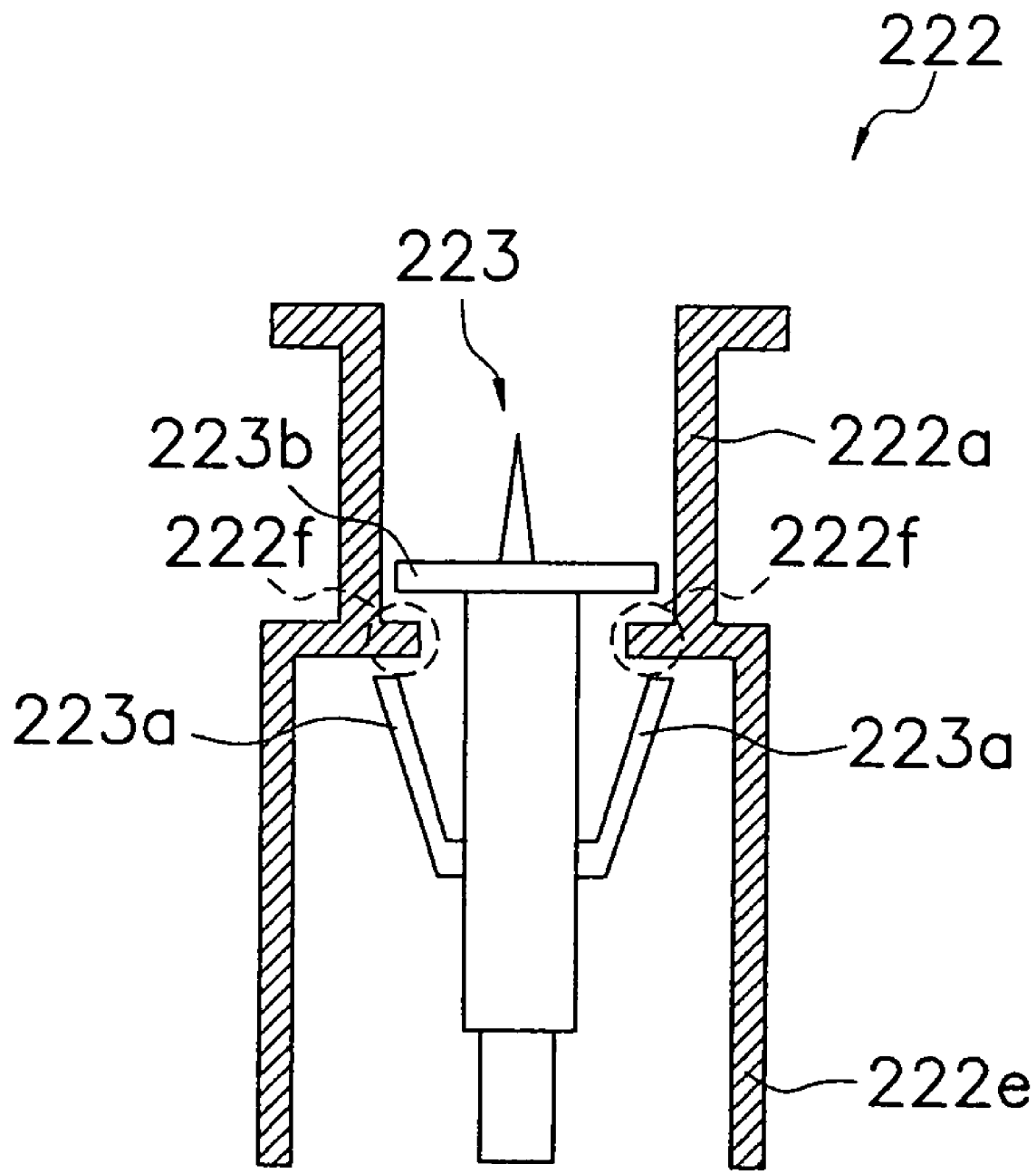
FIG. 19 is a cross sectional view showing a structure where a lancet and a casing according to still another embodiment of the present invention are combined.

Moreover, as in a casing 222 shown in FIG. 19, an outer wall portion 222e may be provided. With such a structure, it becomes possible to prevent disengagement of fitting for holding a puncture body 223 in a tubular portion 222a of a casing 222, which may be caused by erroneously contacting the elastic arm members 223a when they are being packed in a box for transportation or after puncturing. Further, in the example shown in FIG. 19, a convex portion 222f of the casing 222 is fitted by being inserted between a collar portion 223b of the puncture body 223 and the elastic arm members 223a.

(I)

In the above embodiment, fitting between the casing 22 and the puncture body 23 after puncturing is achieved by combining the first tapered portion 22d formed on the inner peripheral surface side of the casing 22 and the groove 23c formed on the outer peripheral surface of the puncture body 23. However, the present invention is not limited to such an example.

Figure 17A:
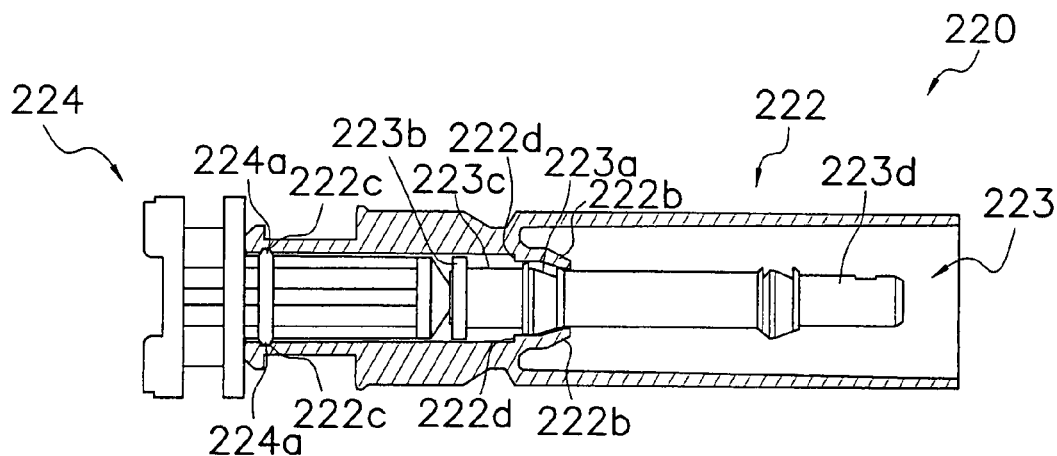
FIGS. 17A through 17C are cross sectional views showing inside a lancet according to yet another embodiment of the present invention before puncturing, during puncturing, and after puncturing.
Figure 18:
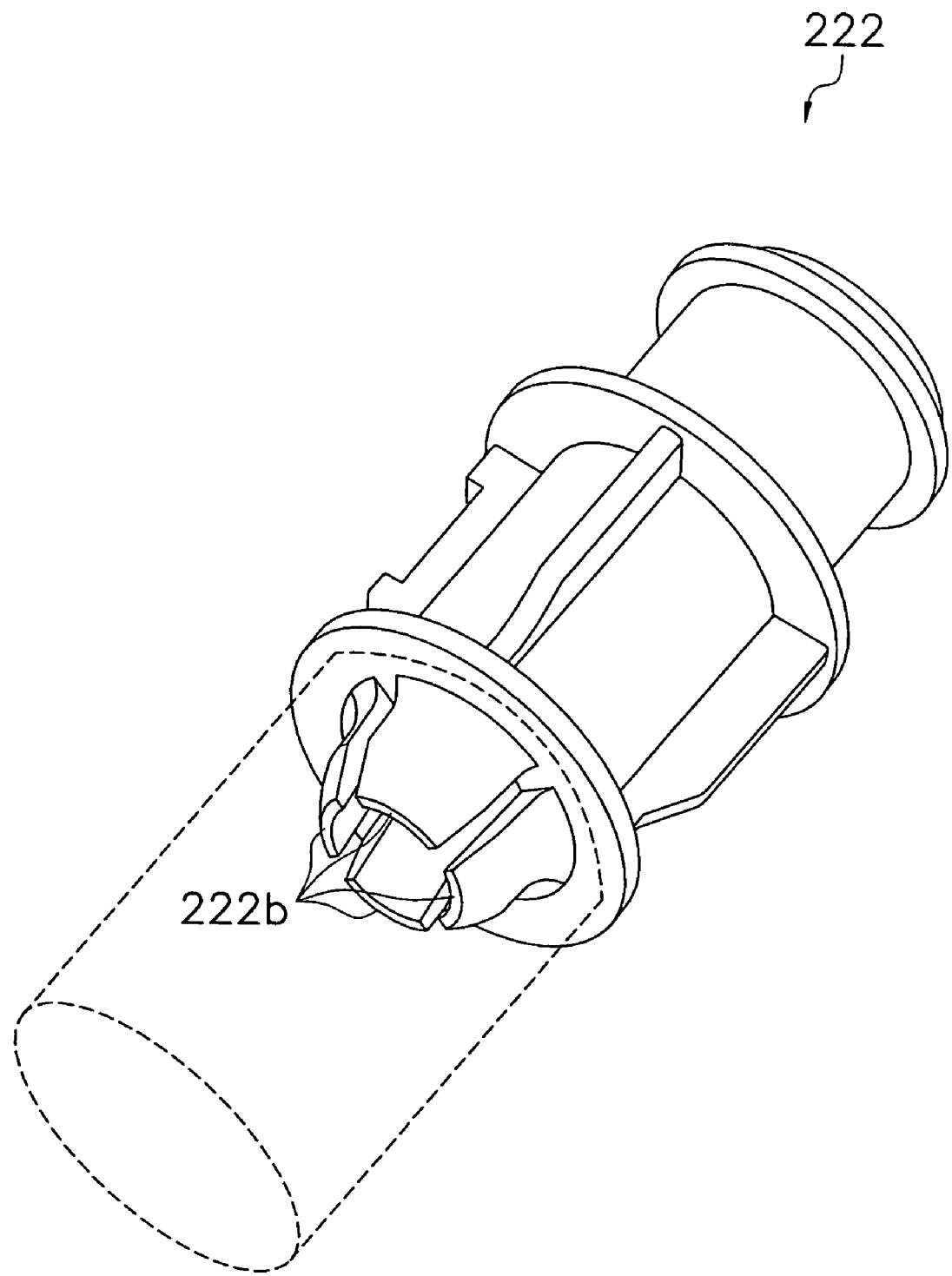

For example, as shown in FIG. 18, a lancet 220 (see FIG. 17A and the like) having an elastic member (first fitting portion) 222b of the casing 222 which resiliently deforms in a direction orthogonal to the puncturing direction and fit to a portion of the puncture body 223 (see FIG. 17A and the like) may be used.

Hereinafter, a specific way of fitting will be described with reference to FIGS. 17A through 17C.

First, as shown in FIG. 17A, in the lancet 220 before puncturing, the puncture body 223 is held in the casing 222 by fitting between a convex portion (second fitting portion) 224a of a cap 224 and a groove (second fitting portion) 222c formed on an inner peripheral surface of the casing 222. Then, when the lancet 220 is loaded to the main body part, which is not shown, an insertion portion 223d on the rear end of the puncture body 223 is held at the main body part more strongly than the fitting between the cap 224 and the casing 222. Thus, for starting use, the cap 224 can be removed without releasing the puncture body 223.

Figure 17B:
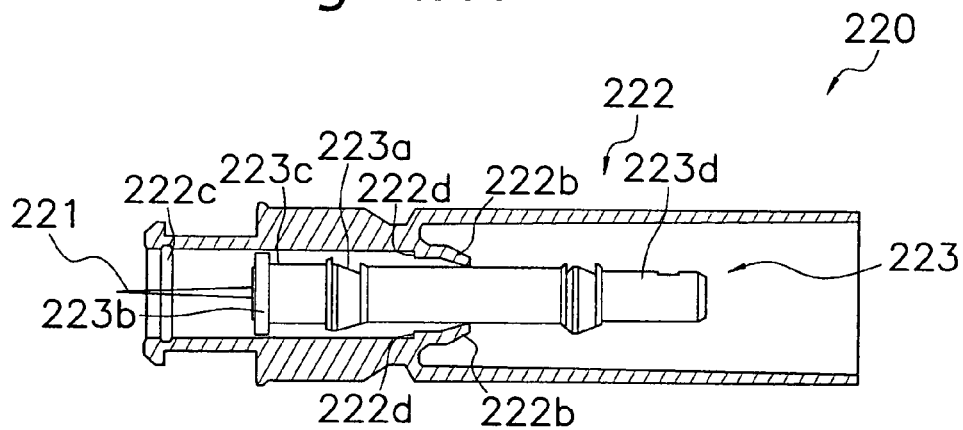
Figure 17C:
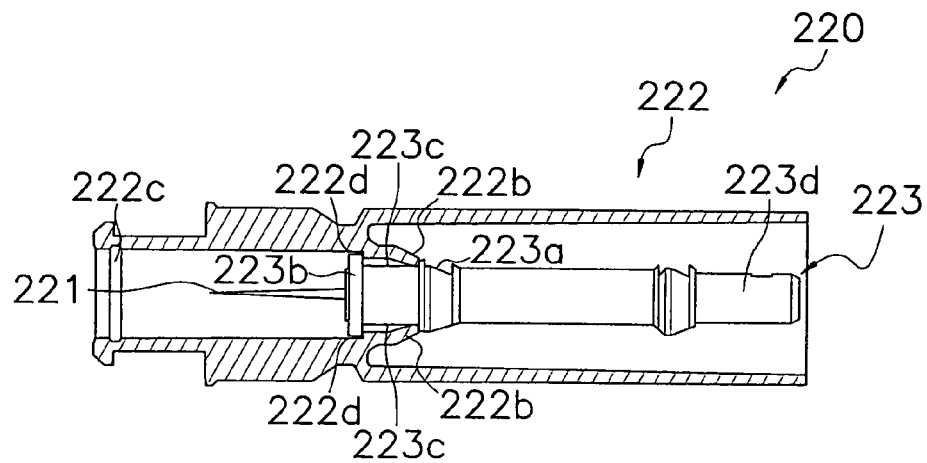

Next, for puncturing, as shown in FIG. 17B, the puncture body 223 is not fitted to the casing 222. Thus, when it receives a biasing force from the main body part, it can move toward the front end in the puncturing direction to puncture. At this state, since the insertion portion 223d on the rear end of the puncture body 223 is held in the lancet holder on the main body part, a puncture needle 221 does not abruptly protrudes from the tip of the casing 222.

After puncturing, the detachment portion on the main body part, which is not shown, is moved toward the front end in the puncturing direction to move the casing 222 toward the front end in the puncturing direction relatively to the puncture body 223. Then, as shown in FIG. 17C, the elastic member 222b formed on the inner periphery of the casing 222 resiliently deforms in a direction orthogonal to the puncturing direction, and run on the tapered portion 223a of the puncture body 223 until it fit to a groove (first fitting portion) 223c. At this state, a flange portion 223b formed at the tip of the puncture body 223 is locked onto a convex portion 222d formed on an end of the elastic member 222b of the casing 222 on the front end side in the puncturing direction. Thus, the puncture body 223 is held in the casing 222 so as to be immovable in the puncturing direction.

INDUSTRIAL APPLICABILITY

The lancet and the lancet device according to the present invention have an effect that a high safety, particularly, safety after use is achieved with a simple structure, and thus, they are widely applicable to puncture devices used in various fields.

The invention claimed is:

1. A lancet to be detachably attached to a main body portion of a lancet device, the lancet device including a biasing member configured to cause a tip of a puncture needle to protrude in a predetermined puncturing direction, the lancet comprising:
   a puncture body including a puncture needle and a connection portion which is formed on an end opposite to the puncture needle and is releasably connected to the main body portion of the lancet device;
   a case portion including a tubular portion which accommodates the puncture body so as to be movable back and forth in the puncturing direction, and an opening formed on an end such that the puncture needle protrudes through the opening; and
   a first fitting portion formed on the tubular portion of the case portion and being disconnected from the puncture body prior to puncturing use and holding the puncture body within the case portion so as to be immovable back and forth in the puncturing direction after puncturing use when the connection portion of the puncture body is released from the main body portion of the lancet device after puncturing use.

2. The lancet according to claim 1, further comprising a second fitting portion configured to hold the puncture body so as to be immovable back and forth in the puncturing direction before use.

3. The lancet according to claim 2, wherein the second fitting portion is formed by combining a convex portion and a recessed portion formed on a cap portion attached to a front end side of the puncture body so as to cover a tip of the puncture needle and an inner surface of the tubular portion.

4. The lancet according to claim 3, wherein the cap portion is integrally formed with the puncture body.

5. The lancet according to claim 1, wherein the first fitting portion has a strong fitting force to prohibit the puncture needle to again move in the puncturing direction.

6. The lancet according to claim 1, wherein the first fitting portion holds the puncture body at a position closer to a portion connected to the main body than a standby position of the puncture body immediately before being discharged so that a tip of the puncture needle protrudes from the opening.

7. The lancet according to claim 1, wherein the first fitting portion is formed by combining a convex portion and a recessed portion formed on an outer peripheral surface of the puncture body substantially parallel to the puncturing direction and an inner peripheral surface of the case portion in which the puncture body moves.

8. The lancet according to claim 7, wherein at least one the convex portion and the recessed portion resiliently deforms to fit to each other.

9. The lancet according to claim 1, wherein the first fitting portion includes:

a recessed portion which is formed on an outer periphery of the puncture body and is formed adjacent to a protrusion of a tapered shape becoming narrower toward the side connected to the main body; and
a convex portion which is formed on an inner surface of the tubular portion and fits to the recessed portion.

10. The lancet according to claim 1, comprising a tapered portion formed on either an outer periphery portion of the puncture body or an inner peripheral surface of the tubular portion.

11. The lancet according to claim 1, wherein the first fitting portion includes:
a convex portion formed on an outer periphery portion of the puncture body; and
a recessed portion which is provided adjacent to a tapered portion formed on an inner surface of the tubular portion and fits to the convex portion.

12. The lancet according to claim 1, wherein the first fitting portion includes:
a recessed portion which is formed adjacent to a plurality of protrusions protruding toward a direction orthogonal to the puncturing direction on an outer peripheral surface of the puncture body; and
a convex portion which is formed on an inner surface of the tubular portion and fits to the recessed portion.

13. The lancet according to claim 1, wherein the first fitting portion includes:
a plurality of convex portions protruding toward a direction orthogonal to the puncturing direction on an outer peripheral surface of the puncture body; and
a recessed portion which is formed on an inner cylindrical surface of the tubular portion and fits to the convex portions.

14. The lancet according to claim 1, wherein the first fitting portion includes a convex portion which is formed to protrude in a direction orthogonal to the puncturing direction from an outer periphery of the puncture body, and has a cross section cut along a plane perpendicular to the puncturing direction which is an ellipsoidal shape.

15. The lancet according to claim 1, further comprising an analysis tool which is attached to an end of the case portion on the front side in the puncturing direction, and analyzes a particular component in body fluid collected from a puncture wound formed by the puncture needle.

16. A lancet device, comprising:
a lancet according to claim 1;
a main body portion including a puncture body holder configured to hold a rear end side of the puncture body with the lancet being loaded, and a biasing member configured to discharge the puncture body with the puncture body holder in the puncturing direction; and
a third fitting portion configured to hold the puncture body and the puncture body holder in the puncturing direction.

17. The lancet device according to claim 16, wherein the third fitting portion has a fitting force configured to hold the puncture body which is weaker than that of the first fitting force.

18. The lancet device according to claim 16, wherein:
the lancet has a second fitting portion formed of a cap portion configured to cover a tip of the puncture needle and the puncture body, in order to hold the puncture body in the case portion before use; and
the third fitting portion has a fitting force stronger than that of the second fitting portion.

19. The lancet device according to claim 16, wherein the third fitting portion includes:
a groove portion formed on an outer peripheral surface of the puncture body which is substantially parallel to the puncturing direction; and
a protrusion which is formed on the puncture body holder of the main body portion, and fits to the groove portion.

20. The lancet device according to claim 16, further comprising a fitting release mechanism configured to release fitting at the third fitting portion.

21. The lancet device according to claim 19, wherein the protrusion is formed on a tip of the puncture body holder via an elastic member having elasticity in a direction orthogonal to the puncturing direction.

22. The lancet device according to claim 19, wherein the puncture body further includes an insertion portion which is formed adjacent to the groove portion on a side connected to the main body portion and becomes narrower toward the side connected to the main body portion.

23. The lancet according to claim 1, wherein the first fitting portion is formed of:
a plurality of elastic members which are provided on an outer peripheral portion of the puncture body and resiliently deform in a direction orthogonal to a puncturing direction; and
a recessed portion which is formed on an inner periphery of the case portion and to which the elastic members fit.

24. The lancet according to claim 23, wherein, configured to the puncture body from the main body portion, the puncture body moves relatively to the case portion in the puncturing direction, and the elastic members contact a part of the case portion and resiliently deform in the direction orthogonal to the puncturing direction so that the elastic members and the recessed portion fit each other.

25. The lancet according to claim 23, wherein the first fitting portion also functions as a second fitting portion configured to hold the puncture body in the case portion before puncturing.

26. The lancet according to claim 25, wherein, configured to attach the puncture body to the main body portion, the elastic members contact a part of the main body portion and resiliently deform in the direction orthogonal to the puncturing direction, and the puncture body moves relatively to the case portion in the puncturing direction to disengage the elastic members and the recessed portion.

27. The lancet according to claim 23, wherein the casing has a wall portion provided so as to cover the elastic members of the puncture body.

28. The lancet according to claim 1, wherein the first fitting portion is formed by combining a recessed portion formed between a plurality of elastic members which are provided on an outer peripheral portion of the puncture body and resiliently deform in a direction orthogonal to the puncturing direction and a collar portion formed on a tip of the puncture body, and a convex portion formed on an inner peripheral surface side of the case portion.

29. The lancet according to claim 1, wherein the first fitting portion is formed by combining an elastic member formed in the case portion and resiliently deforms in a direction orthogonal to the puncturing direction, and a recessed portion formed on an outer peripheral portion of the puncture body.

30. The lancet according to claim 28 wherein a cross section of the puncture body along the direction orthogonal to the puncturing direction has a circular shape.

31. The lancet according to claim 29, wherein the puncture body further includes a tapered portion located so as to be adjacent to the recessed portion.

32. A lancet to be detachably attached to a main body portion of a lancet device, the lancet device including a biasing member configured to cause a tip of a puncture needle to protrude in a predetermined puncturing direction, the lancet comprising:
- a puncture body including a puncture needle and a connection portion which is formed on an end opposite to the puncture needle and is connected to the main body of the lancet device;
- a case portion including a tubular portion which accommodates the puncture body so as to be movable back and forth in the puncturing direction, and an opening formed on an end thereof such that the puncture needle protrudes through the opening;
- a cap portion removably fitted to the case portion such that when the cap portion is fitted to the case portion, the cap portion conceals the puncture needle and when the cap portion is removed the puncture needle is exposed and ready for puncturing use; and
- a first fitting portion formed on the case portion and being disconnected from the puncture body prior to puncturing use holding the puncture body in the case portion so as to be immovable back and forth in the puncturing direction when the connection portion of the puncture body is separated from the main body portion of the lancet device.

* * * * *